(12) United States Patent
Tavana et al.

(10) Patent No.: US 10,119,107 B2
(45) Date of Patent: Nov. 6, 2018

(54) AUTOMATED CELL AND TISSUE BIOPRINTER

(71) Applicants: Hossein Tavana, Hudson, OH (US); David Petrak, Cuyahoga Falls, OH (US)

(72) Inventors: Hossein Tavana, Hudson, OH (US); David Petrak, Cuyahoga Falls, OH (US)

(73) Assignee: The University of Akron, Akron, OH (US)

( * ) Notice: Subject to any disclaimer, the term of this patent is extended or adjusted under 35 U.S.C. 154(b) by 152 days.

(21) Appl. No.: 14/890,998

(22) PCT Filed: May 30, 2014

(86) PCT No.: PCT/US2014/040196
§ 371 (c)(1),
(2) Date: Nov. 13, 2015

(87) PCT Pub. No.: WO2014/194180
PCT Pub. Date: Dec. 4, 2014

(65) Prior Publication Data
US 2016/0083681 A1  Mar. 24, 2016

Related U.S. Application Data

(60) Provisional application No. 61/828,924, filed on May 30, 2013.

(51) Int. Cl.
*C12M 3/00* (2006.01)
*B01L 3/02* (2006.01)
(Continued)

(52) U.S. Cl.
CPC ........... *C12M 21/08* (2013.01); *B01L 3/0268* (2013.01); *B29C 67/0059* (2013.01);
(Continued)

(58) Field of Classification Search
None
See application file for complete search history.

(56) References Cited

U.S. PATENT DOCUMENTS 9,244,057 B2  1/2016  Takayama et al.
9,469,869 B2  10/2016  Takayama et al.
(Continued)

FOREIGN PATENT DOCUMENTS

WO  WO-2013040078 A2 *  3/2013  ............. A61L 27/34

OTHER PUBLICATIONS

Tavana et al. Polymeric aqueous biphasic systems for non-contact cell printing on cells: engineering heterocellular embryonic stem cell niches, Adv Mater. Jun. 25, 2010 (Jun. 25, 2010), vol. 22, pp. 2628-2631. (Year: 2010).*
(Continued)

*Primary Examiner* — Alison L Hindenlang
*Assistant Examiner* — Jamel M Nelson
(74) *Attorney, Agent, or Firm* — Renner Kenner Greive Bobak Taylor & Weber

(57) ABSTRACT

The present invention are directed to a novel automated cell bioprinter and related methods for making three-dimensional tissue constructs with spatial organization of cells that provides: (i) organized cell placement and spatial assembly of multiple cell types in a reproducible manner (ii) direct and non-contact assembly of multiple cell types and/or cell layers without exerting damaging forces on the cells or tissues, (iii) retention of cell viability and functionality during assembly steps and long periods of culture, (iv) minimal use of harmful and toxic chemicals such as profuse amounts of mineral oil and buffer reagent, and (v) efficient layer-to-layer assembly of cell layers within the three-dimensional construct while (vi) avoiding the use of complicated surface treatments that prevents scale-up, and (vii)
(Continued)

avoiding mutation-inducing radiations such as UV used to photocrosslink hydrogels.

16 Claims, 19 Drawing Sheets

(51) Int. Cl.

| | | |
|---|---|---|
| *B29C 67/00* | (2017.01) | |
| *C12M 1/00* | (2006.01) | |
| *C12M 1/26* | (2006.01) | |
| *B33Y 10/00* | (2015.01) | |
| *B33Y 30/00* | (2015.01) | |
| *B33Y 50/02* | (2015.01) | |
| *B33Y 70/00* | (2015.01) | |
| *B29L 31/00* | (2006.01) | |

(52) U.S. Cl.
CPC ...... *B29C 67/0088* (2013.01); *B29K 2005/00* (2013.01); *B29L 2031/7532* (2013.01); *B33Y 10/00* (2014.12); *B33Y 30/00* (2014.12); *B33Y 50/02* (2014.12); *B33Y 70/00* (2014.12); *C12M 23/50* (2013.01); *C12M 33/00* (2013.01)

(56) References Cited

U.S. PATENT DOCUMENTS

| | | | |
|---|---|---|---|
| 2009/0263849 A1* | 10/2009 | Sun | B01L 3/502707 |
| | | | 435/29 |
| 2011/0177590 A1* | 7/2011 | Clyne | A61L 27/38 |
| | | | 435/325 |
| 2012/0089238 A1* | 4/2012 | Kang | A61L 27/20 |
| | | | 623/23.72 |
| 2012/0116568 A1 | 5/2012 | Murphy et al. | |

OTHER PUBLICATIONS

Tavana et al. "Nanolitre liquid patterning in aqueous environments for spatially defined reagent delivery to mammalian cells," Nat Mater. Aug. 16, 2009 (Aug. 16, 2009), vol. 8, pp. 736-741. (Year: 2009).*

Thomasnet. "Benchtop Platform provides active vibration isolation," Thomasnet News, Aug. 2005 (Aug. 18, 2005), Retrieved from the Internet: <http://news.thomasnet.com/print_friendly.html?prid=466526> on Sep. 22, 2014 (Sep. 22, 2014). entire document.

Tavana et al. "Aqueous biphasic microprinting approach to tissue engineering," Biomicrofluidics. Mar. 30, 2011 (Mar. 30, 2011). vol. 5, pp. 1-8. entire document.

* cited by examiner

FIG. 14A
FIG. 14B
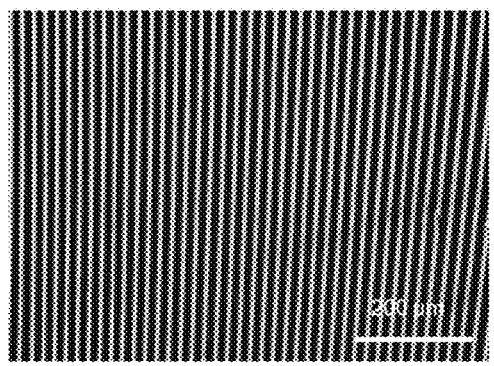
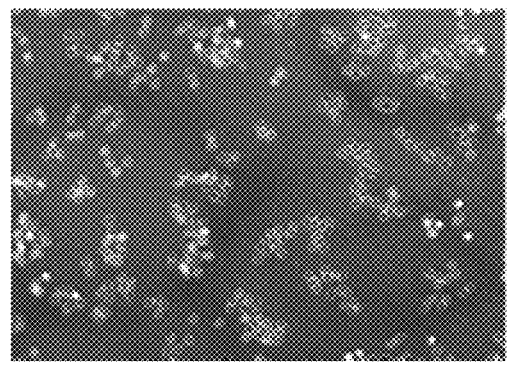
FIG. 14C
FIG. 14D
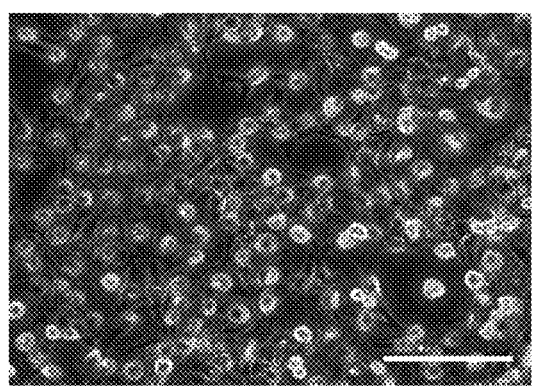
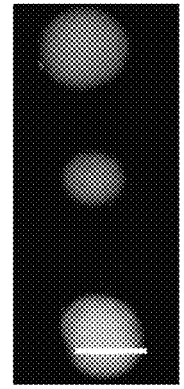

AUTOMATED CELL AND TISSUE BIOPRINTER

CROSS REFERENCE TO RELATED APPLICATIONS

This application claims the benefit of International Application No. PCT/US2014/40196, entitled "Automated Cell and Tissue Bioprinter," filed May 30, 2014, which claims the benefit of U.S. provisional patent application Ser. No. 61/828,924 entitled "Cell and Tissue Bioprinter," filed May 30, 2013, and incorporated herein by reference in its entirety.

FIELD OF THE INVENTION

One or more embodiments of the present invention relates to the area of tissue engineering and more specifically, to an automated mechanisms and related methods for making three-dimensional tissue constructs with spatial organization of cells using a polymeric aqueous two-phase system.

BACKGROUND OF THE INVENTION

Tissue engineering is an emerging field that aims to create biological substitutes for diseased or damaged tissues. A major challenge in the field of tissue engineering is creating two- and three-dimensional multi-cellular constructs with defined spatial organization of cells, to mimic the architecture of living tissues, where homotypic and heterotypic cellular interactions are key to tissue formation and function.

Current tissue engineering approaches focus on creating multi-cellular constructs from either the top-down or bottom-up. Both approaches seek to provide a supportive niche for cells to guide their proliferation, differentiation, and maturation and generate functional constructs. Although both classes show some promise, bottom-up approaches can potentially overcome limitations in cell placement and alignment that are difficult to achieve in most top-down approaches. Recently, a non-contact patterning method based on the use of aqueous two-phase systems has been adopted to autonomously dispense a suspension of cells without any actuation forces. See e.g. Tavana, H.; et al., Nanoliter liquid patterning in aqueous environments for spatially defined reagent delivery for mammalian cells. *Nature Materials.* 8, 736-41 (2009) and Tavana, H.; et al., Polymeric aqueous biphasic systems for non-contact cell printing on cells: engineering heterocellular embryonic stem cell niches. *Adv Mater* 2010, 22 (24), 2628-31, the disclosures of which are hereby incorporated by reference in their entirety. Unfortunately, these systems showed only the capability to print bioreagents and cells in arbitrary shapes, because printing was performed with manual liquid handling tools, it could only control droplet-shaped patterns.

What is needed in the art is an automated mechanism and related method for making three-dimensional tissue constructs with spatial organization of cells that provides: (i) organized cell placement and spatial assembly of multiple cell types in a reproducible manner (ii) direct and non-contact assembly of multiple cell types and/or cell layers without exerting damaging forces on the cells or tissues, (iii) retention of cell viability and functionality during assembly steps and long periods of culture, (iv) minimal use of harmful and toxic chemicals such as profuse amounts of mineral oil and buffer reagent, and (v) efficient layer-to-layer assembly of cell layers within the three-dimensional construct while (vi) avoiding the use of complicated surface treatments that prevents scale-up, and (vii) avoiding mutation-inducing radiations such as UV used to photocrosslink hydrogels.

SUMMARY OF THE INVENTION

One or more embodiments of the present invention are directed to an automated mechanism and related methods for making three-dimensional tissue constructs with spatial organization of cells that provides: (i) organized cell placement and spatial assembly of multiple cell types in a reproducible manner (ii) direct and non-contact assembly of multiple cell types and/or cell layers without exerting damaging forces on the cells or tissues, (iii) retention of cell viability and functionality during assembly steps and long periods of culture, (iv) minimal use of harmful and toxic chemicals such as profuse amounts of mineral oil and buffer reagent, and (v) efficient layer-to-layer assembly of cell layers within the three-dimensional construct while (vi) avoiding the use of complicated surface treatments that prevents scale-up, and (vii) avoiding mutation-inducing radiations such as UV used to photocrosslink hydrogels.

In a first aspect, the present invention provides an apparatus for bioprinting cells on a surface comprising: a cell monolayer or biomaterial surface upon which a plurality of cells are to be printed; one or more printing tips; a cartridge for holding said one or more printing tips; and a three-axis motion control system configured to move said cartridge in three dimensions with respect to said cell monolayer or biomaterial surface.

In one or more embodiments, the apparatus for bioprinting cells further comprises: a stabilized platform; a container for holding said cell monolayer or biomaterial surface; a printing stage configured to mate with and secure a holder for securing the container to the printing stage.

In one or more embodiments, the apparatus for bioprinting cells includes any one or more of the above referenced embodiments of the first aspect of the present invention further comprising an extension arm extending from said three-axis motion control system and holding said cartridge, wherein said extension arm permits cartridge motion over the cell monolayer or biomaterial surface.

In one or more embodiments, the apparatus for bioprinting cells includes any one or more of the above referenced embodiments of the first aspect of the present invention wherein said cell monolayer or biomaterial surface is selected from the group consisting of a 95-100% confluent cell monolayer of any cell type, a decellularized matrix, and combinations thereof.

In one or more embodiments, the apparatus for bioprinting cells includes any one or more of the above referenced embodiments of the first aspect of the present invention wherein said cartridge holds from 1 to 6 printing tips. In one or more embodiments, the apparatus for bioprinting cells includes any one or more of the above referenced embodiments of the first aspect of the present invention wherein said printing tips have an internal diameter of from about 200 to about 750 um. In one or more embodiments, the apparatus for bioprinting cells includes any one or more of the above referenced embodiments of the first aspect of the present invention wherein said printing tips have an internal diameter of from about 200 to about 300 um. In one or more embodiments, the apparatus for bioprinting cells includes any one or more of the above referenced embodiments of the first aspect of the present invention wherein said printing tips have loading volume over 6 μL.

In one or more embodiments, the apparatus for bioprinting cells includes any one or more of the above referenced embodiments of the first aspect of the present invention wherein said three-axis motion control system comprises: a first motor for moving said cartridge in two directions on a first horizontal slide along an x axis; a second motor for moving said cartridge in two directions on a second horizontal slide along an y axis; a third motor for moving said cartridge in two directions on a vertical slide along an z axis; one or more controllers in communication with one or more of said first motor, second motor, and third motor; and a computer electrically connected to each of said one or more controllers, wherein said computer is configured to provide pre-programmed instructions to said one or more controllers to simultaneously direct the movement of said first motor, said second motor, and said third motor.

In one or more embodiments, the apparatus for bioprinting cells includes any one or more of the above referenced embodiments of the first aspect of the present invention wherein said three-axis motion control system is configured to move said cell monolayer or biomaterial surface in three dimensions with respect to said one or more printing tips.

In a second aspect, the present invention also provides method for bioprinting cells using the above apparatus comprising: preparing an aqueous cell containing medium containing a first aqueous polymer; loading said aqueous cell containing medium into the one or more printing tips preparing a second aqueous polymer solution, wherein said second aqueous polymer solution is less dense than and immiscible with said aqueous cell containing medium so that when the second aqueous polymer solution and aqueous cell containing medium are mixed a partition is formed there between with the aqueous polymer solution partitioned on the top and the aqueous cell containing medium; preparing a monolayer or biomaterial surface upon which the cells contained in said aqueous cell containing medium are to be printed; covering said monolayer or biomaterial surface with said second aqueous polymer solution to a depth of from about 1 to about 15 mm; inserting said one or more printing tips into openings in said cartridge configured to receive said printing tips; programming the three-axis motion control system to move said cartridge in three dimensions and at a predetermined speed to place the printing tips at specific predetermined locations as the aqueous cell containing medium is dispensed onto the monolayer or biomaterial surface; and dispensing the aqueous cell containing medium onto the cell monolayer or biomaterial surface at specific predetermined locations and at a predetermined speed.

In one or more embodiments, the method for bioprinting cells includes the above referenced embodiments of the second aspect of the present invention wherein said first polymer is dextran. In one or more embodiments, the method for bioprinting cells includes any one or more of the above referenced embodiments of the second aspect of the present invention wherein said aqueous polymer solution contains polyethylene glycol (PEG).

In one or more embodiments, the method for bioprinting cells includes any one or more of the above referenced embodiments of the second aspect of the present invention wherein the interfacial tension between the second aqueous polymer solution and the aqueous cell containing medium is from about 10 to about 14 µN/m. In one or more embodiments, the method for bioprinting cells includes any one or more of the above referenced embodiments of the second aspect of the present invention wherein and the interfacial tension between the second aqueous polymer solution and the aqueous cell containing medium is 12 µN/m. In one or more embodiments, the method for bioprinting cells includes any one or more of the above referenced embodiments of the second aspect of the present invention wherein the cells are selected from the cell types consisting of MDA-MB-231 breast cancer cells, C2C12 mouse myoblast cells, and combinations thereof.

In one or more embodiments, the method for bioprinting cells includes any one or more of the above referenced embodiments of the second aspect of the present invention wherein the cells are dispensed from said printing tips by the force of gravity.

In one or more embodiments, the method for bioprinting cells includes any one or more of the above referenced embodiments of the second aspect of the present invention further comprising: allowing the cells in said aqueous cell containing medium to adhere to the cell monolayer or biomaterial surface; rinsing any unadhered cells off said the monolayer or biomaterial surface; covering said the cell monolayer or biomaterial surface and any cells adhered thereto with said second aqueous polymer solution to a depth of from about 1 to about 15 mm and repeating these steps to apply a second layer of aqueous cell-containing medium upon said cell monolayer or biomaterial surface. The method of claim 17 further comprising: repeating these steps to apply additional cells upon said cell monolayer or biomaterial surface and/or previously adhered cells to produce a three dimensional array of cells.

In one or more embodiments, the method for bioprinting cells includes any one or more of the above referenced embodiments of the second aspect of the present invention wherein said cell monolayer or biomaterial surface is selected from the group consisting of a 95-100% confluent cell monolayer of any cell type, a decellularized matrix, and combinations thereof.

In one or more embodiments, the method for bioprinting cells includes any one or more of the above referenced embodiments of the second aspect of the present invention further comprising dispensing the aqueous cell containing medium onto the cell monolayer or biomaterial surface in one or more linear patterns. In one or more embodiments, the method for bioprinting cells includes any one or more of the above referenced embodiments of the second aspect of the present invention wherein said one or more linear patterns are reproducible. In one or more embodiments, the method for bioprinting cells includes any one or more of the above referenced embodiments of the second aspect of the present invention wherein said one or more linear patterns are stable. In one or more embodiments, the method for bioprinting cells includes any one or more of the above referenced embodiments of the second aspect of the present invention wherein each of said one or more linear patterns has a width of from about 254 µm to about 386 µm. In one or more embodiments, the method for bioprinting cells includes any one or more of the above referenced embodiments of the second aspect of the present invention wherein said each of said one or more linear patterns has a printing resolution of from 257.5 µm to about 386.5 µm. In one or more embodiments, the method for bioprinting cells includes any one or more of the above referenced embodiments of the second aspect of the present invention wherein the Laplace Pressure is 130 mPa or less.

BRIEF DESCRIPTION OF THE DRAWINGS

For a more complete understanding of the features and advantages of the present invention, reference is now made to the detailed description of the invention along with the accompanying figures in which:

FIG. 8A is a schematic showing preparation of the aqueous cell containing medium (bioink) for use with some embodiments of the present invention and shows mixing the DEX phase with cell suspension. The bioink is then loaded into the printing tips. FIG. 8B is a schematic showing preparation of the biopaper printing surface and includes immersing a monolayer of cells or decellularized matrix in the PEG phase. FIG. 8C is a schematic showing a side view of a printing process according to at least one embodiment of the present invention. Printing tips are loaded into the cartridge. The cartridge is then programmed to descend into PEG solution resulting in autonomous dispensing of the bio-ink.

FIG. 9A is a schematic representation of balance between the three interfacial tension terms at the interface of PEG-DEX-cells. The schematic shows a cross-sectional view of a printed line. FIG. 9B is an image showing a side view of droplet of the DEX phase in the PEG phase according to some embodiments of the present invention. Printed patterns have an average thickness of 25 µm.

FIG. 10A is an image showing a printing tip of 300 µm inner diameter loaded with FITC-DEX; the arrow indicates the region above the capillary. FIG. 10B is a graph showing how printed patterns width changes linearly with the height of reagent above the capillary portion, within the volume range studied. Asterisks indicate data sets statistically different from each other ($p<0.05$).

FIG. 11A is a sequence of images showing image processing of an unstable linear pattern of FITC-DEX, representing Plateau-Rayleigh Instability. FIG. 11B shows to images of necking and a graph depicting capillary pressure calculations at the that point of necking. Scale bar 300 µm in 11A and 500 µm in 11B.

FIG. 12A is a graph showing variations of printing pattern width with the lateral speed of tips according to one or more embodiments of the present invention. Printed FITC-DEX patterns show a systematic decrease in width ($R^2=0.98$), a plateau at higher speeds, and instability at beyond 22 mm/s. All prints were done on a monolayer of C2C12 cells as the substrate. FIG. 12B is an image of lines of printed cells showing the variation of cellular pattern width with the tip speed. Scale bar 500 µm in 12B.

FIGS. 14A-H are a series of images showing cell patterns printed on varying substrates. FIG. 14A is an image of cells printed on a PDLA surface decorated with 20 µm microgrooves showing the pattern resolved to droplets of cells. FIG. 14B is an image of cells printed on a 50% confluent cell monolayer showing the pattern resolved to droplets of cells. FIG. 14C is an image of cells printed on a PDMS mold replicate of fixed cells showing the pattern resolved to droplets of cells. FIG. 14D is an image of cells printed on a smooth PDLA, microgrooved PDLA, low cell-density and cell layer replica that quickly became unstable and resolved into droplets. FIG. 14E is an image of cells printed on a decellularized surface generated from a confluent MB-MDA 231 breast cancer cells. FIG. 14F is an image showing fluorescent staining of cells printed on a decellularized matrix using a protein labeling dye FIG. 14G is an image of cells printed on a decellularized matrix surface (showed smoother edges than on a cell monolayer). And FIG. 14H is an image of cells printed on a decellularized matrix (supporting linear cell patterns confirming the long-term stability of patterns). Scale bar: 200 µm in FIGS. 14A, 14B, 14C, 14E, and 14F, 400 µm in FIGS. 14D and 14G, and 300 µm in FIG. 14H.

FIGS. 15D and 15E are user-defined spelling of "UA" (FIG. 15D) and "NEOMED" (FIG. 15E). C2C12 cells were stained with green cell and red cell tracking dyes. Scale bar in FIGS. 15A, 15B, and 15C is 500 µm. The scale bar is 300 µm in FIGS. 15D and 15E.

DETAILED DESCRIPTION OF THE ILLUSTRATIVE EMBODIMENTS

The present invention is generally directed to an apparatus and related methods for the automated printing of cells in a spatially and temporally controlled manner using aqueous two-phase system (ATPS)-based printing technology and may provide (i) three-axis motion control to precisely register coordinates on the printing surface, (ii) sufficient travel range in a horizontal plane to cover the printing surface, (iii) sufficient load-capacity to accommodate additional components such as printing tools, (iv) computer-interface capability, (v) software program compatible with commercially available operating systems, and (vi) a footprint small enough to be housed inside a standard sterile culture hood. Moreover, unlike the few existing cell printing approaches that use external mechanical, thermal, electrical, or fluidic forces to eject cells from a nozzle, printing with ATPS is autonomous without a need for forces that compromise viability of printed cells.

An aqueous two-phase system forms when aqueous solutions of two polymers above certain concentrations are combined. The resulting mixture gives rise to two liquid layers, both of which are highly aqueous (as high as 95%). The top phase is enriched with the polymer with lower density while the bottom phase is enriched with the denser polymer. Phase separation is influenced by a number of physical and chemical properties of the polymers and the aqueous solvent used. Particular properties of significance include the molecular weight of phase-forming polymers and overall charge distribution of polymer chains, temperature of the solutions, and pH and ionic composition of the aqueous solvent. Most significantly, separation is determined by the concentration of each polymer in the aqueous solvent and often occurs at low polymer concentrations, making ATPS suitable for a wide-range of biological applications targeted at the segregation of biomolecules.

Figure 1:
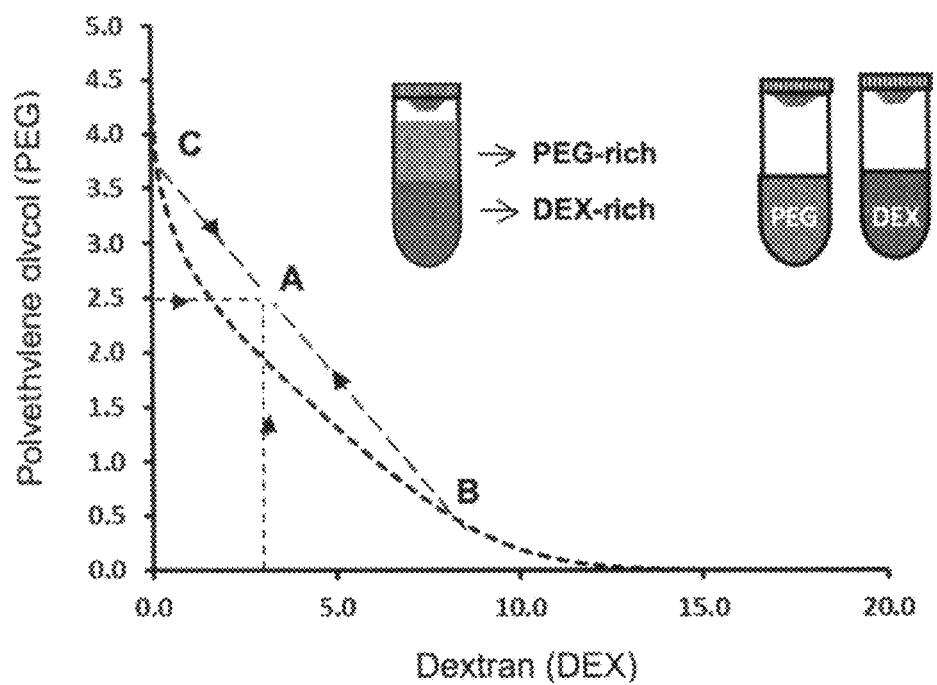
FIG. 1 is a phase diagram of an aqueous two-phase system comprising polyethylene glycol (PEG) and dextran (DEX) as phase forming polymers. Point A represents the initial concentration of each polymer in the entire solution and points C and B represent the compositions of top and bottom phases in equilibrium, respectively. The line connecting all three points is called a tie line and is a unique property of the given two-phase system.

The specific polymer concentrations giving rise to phase separation are described with a phase diagram. A phase diagram uniquely characterizes an ATPS, delineates the range of polymer concentrations above a binodal curve that result in phase separation, and provides the composition of each phase (See, FIG. 1). A phase diagram can experimentally be constructed by creating two separate aqueous solutions, each enriched with a high concentration of a different polymer. A wide range of dilutions from each solution is prepared. Dilutions from one polymeric solution are mixed with those of the second polymeric solutions in conical tubes and allowed to equilibrate and form two separate phases with a sharp interface. The weight of each polymeric solution is measured and recorded. ATPS in each tube is titrated drop-wise with water until a one-phase system forms. The final weight of the conical containing the one-phase system is recorded and used to calculate the weight of diluent added just prior to one-phase formation. A binodal curve is determined through plotting the final composition of each system. FIG. 1 shows the phase diagram of an ATPS consisting of Polyethylene glycol (PEG) with Mw: 35K and dextran (DEX) with Mw: 500K.

Suitable polymer combinations and concentrations may include, without limitation 5-10% PEG, Mw: 8 k, 5-10% DEX(Mw: 500 k); 2.5-10.0% PEG, Mw: 35 k, 3.2-10% DEX 500 k, Mw: 500 k; Dextran-Ficoll, Dextran-benzoyl-dextran, Dextran-poly(vinyl alcohol) (PVA), PVA-PEG, Maltodextrin-PEG, Pullulan-PEG, Poly(vinyl methyl ether)-PEG, and Dextran-poly(ethylene glycol propylene glycol) copolymer (Ucon).

The cells that can be printed using the automated cell bioprinter of embodiments of the present invention are not particularly limited but may include, without limitation, MD-MBA 231 breast cancer cells, C2C12 mouse myoblast cells, mouse embryonic stem cells, rat endothelial cells, human umbilical vein endothelial cells (HUVECs), rat smooth muscle cells, neurons, PA6 stromal cells have all been tested but in principle any cell type can survive in a highly aqueous environment provided they are stored in their cell-specific media.

In one or more embodiments, the present invention is directed to the use of microliter volumes that consists of aqueous dextran (DEX) and polyethylene glycol (PEG) phases, to print cells on various support surfaces. These two polymers were selected due to their ability to quickly dissolve in aqueous media and form ATPS at relatively small concentrations. In these embodiments, the aqueous solutions of DEX and PEG are prepared in complete growth media. Owing to its larger density, the aqueous DEX phase always forms the bottom phase and hence, is used as the printing phase that contains cells. Accordingly, the surface to print on (cell monolayer or biomaterial surface) is maintained in the PEG phase. To achieve efficient cell printing using ATPS, cells must favor and remain confined to the bottom DEX phase.

Cell partition in ATPSs has previously been shown to be mainly a function of the interfacial tension between the two aqueous phases, $\gamma_{12}$, and may be expressed as:

$$-\log K \propto \alpha \gamma_{12}, \quad [1]$$

where K denotes the partition coefficient (i.e., the ratio of the number of cells in the bottom phase to the total number of cells in the top and bottom phases and interface between them) and can vary between 0 and 1. The variable a is an empirical constant. Thus, cell partition to the bottom phase can be easily manipulated by minimizing the interfacial tension, $\gamma_{12}$ between the upper polymer phase (PEG) and the lower printing phase (DEX). The interfacial tension between two phases can be determined either through direct measurements or from a known phase diagram using the following equation:

$$\log \gamma_{12} = A | B \log(TLL), \quad [2]$$

where A and B are experimental constants specific to each individual two-phase system and TLL denotes the tie-line length, shown as $\overline{CB}$ in FIG. 1. The tie-line shows the concentration of each polymer in the top and bottom phases. The lower the polymer concentration of the system, the smaller the tie-line length, and from equation 2, the smaller the two-phase interfacial tension is.

In some embodiments, the polymers used consist of 5.0% (w/w) PEG (Mw: 25K), 6.4% (w/w) DEX (Mw: 500K). In some embodiments, the polymers used consist of 8.0% (w/w) PEG (Mw: 8K), 10.0% (w/w) DEX (Mw: 500K).

In some embodiments, the interfacial tension between the upper polymer phase and the lower printing phase is from about 10 µN/m to about 12 µN/m. In some embodiments, the interfacial tension between the upper polymer phase and the lower printing phase is from about 12 µN/m to about 14 µN/m. In some embodiments, the interfacial tension between the upper polymer phase and the lower printing phase is 12 µN/m. In some embodiments, the partition coefficient of K between the upper polymer phase and the lower printing phase is from about 0.70 to about 0.80. In some embodiments, the partition coefficient of K between the upper polymer phase and the lower printing phase from is about 0.4 to about 0.5. In some embodiments, the partition coefficient of K between the upper polymer phase and the lower printing phase is 0.78.

Referring now to FIG. 1, an automated cell bioprinter is shown, generally indicated by the numeral 2. The general size of the automated cell printer 2 is not particularly limited but can, in at least some embodiments, have a footprint small enough to be housed inside a standard sterile culture hood to provide for printing cells and biomolecules onto different biological surfaces in a sterile environment. In general outline, the automated cell printer 2 of one or more embodiments of the present invention includes a three dimensional bioprinter assembly 4, one or more controllers 6, and a computer 8.

Figure 2:
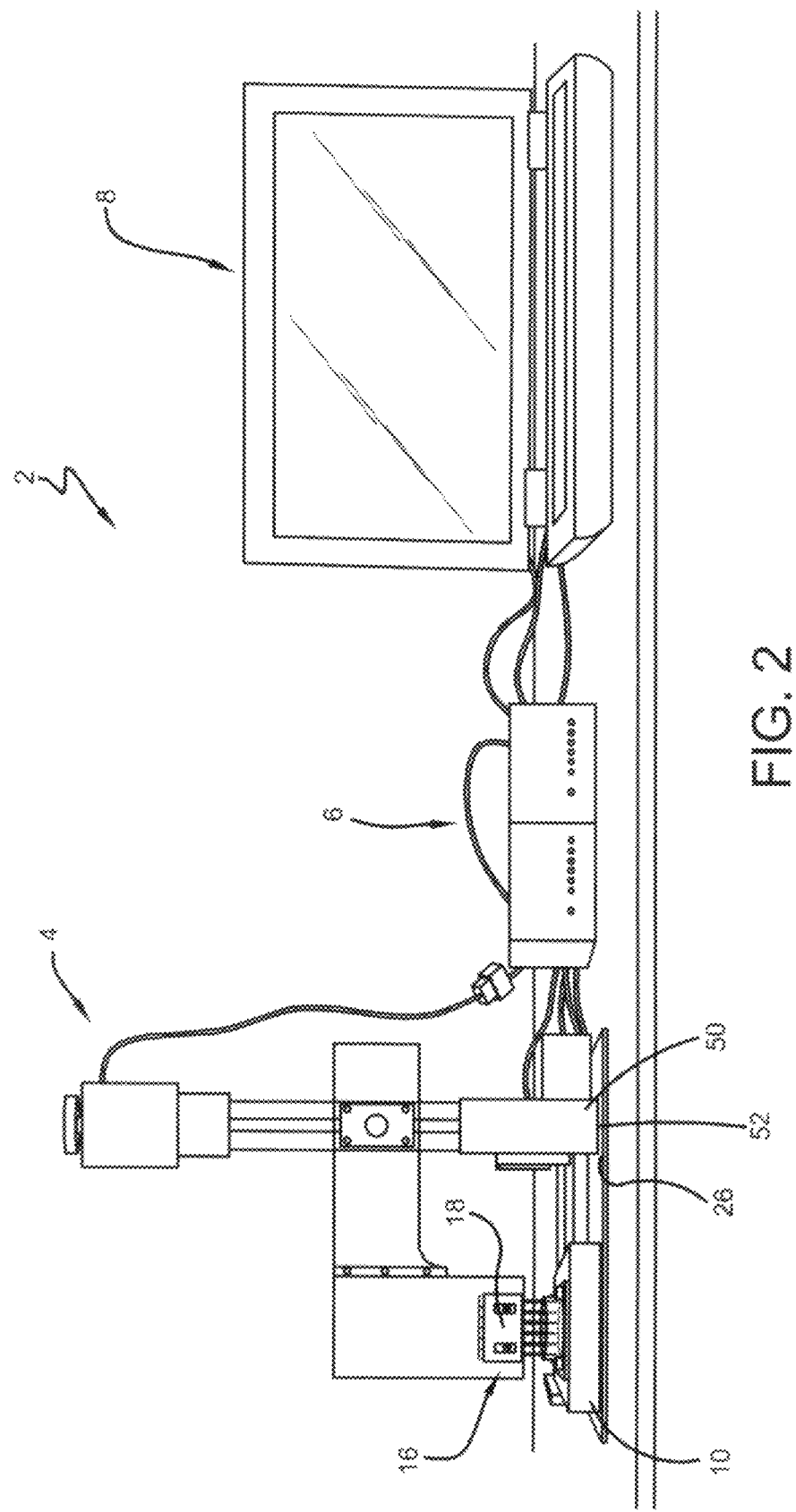
FIG. 2 is a schematic representation of a, automated cell bioprinter according to at least one embodiment of the present invention.
Figure 3:
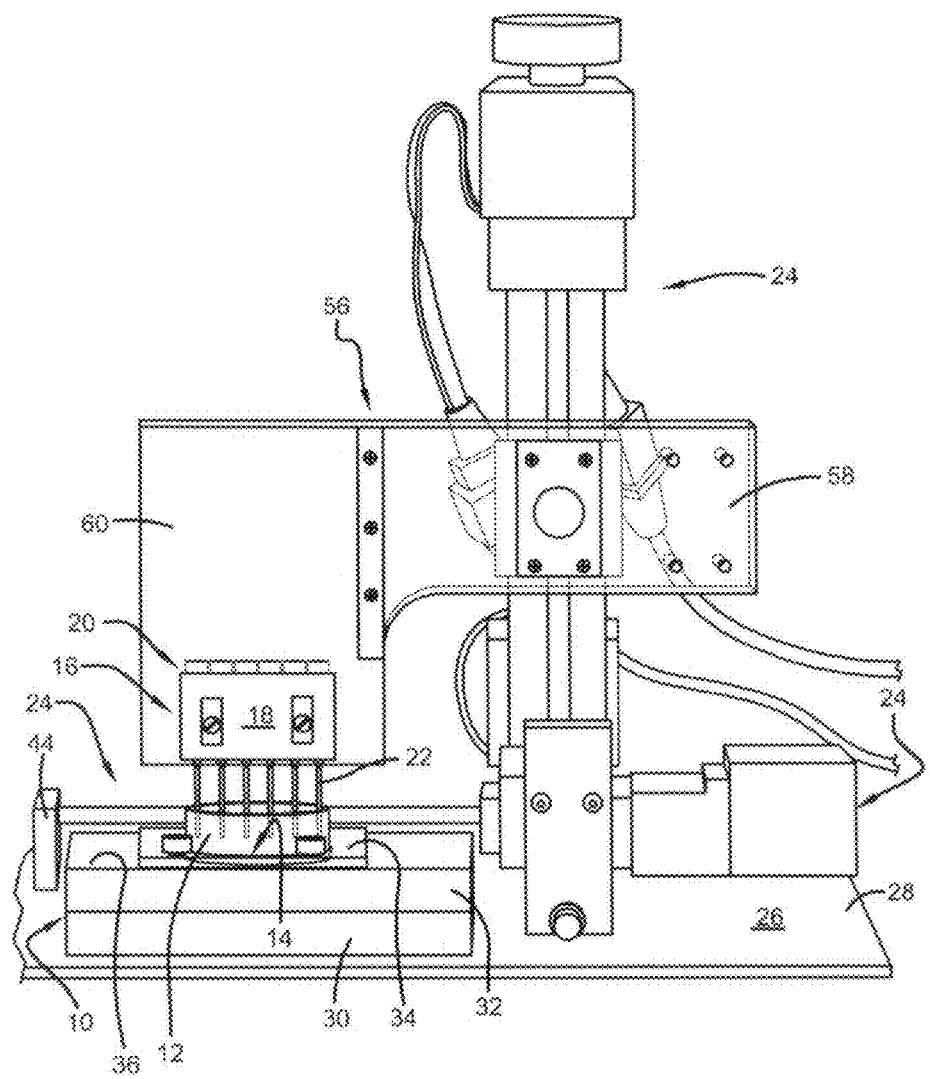
FIG. 3 is a front view of a three dimensional bioprinter assembly according to at least one embodiment of the present invention.
Figure 4:
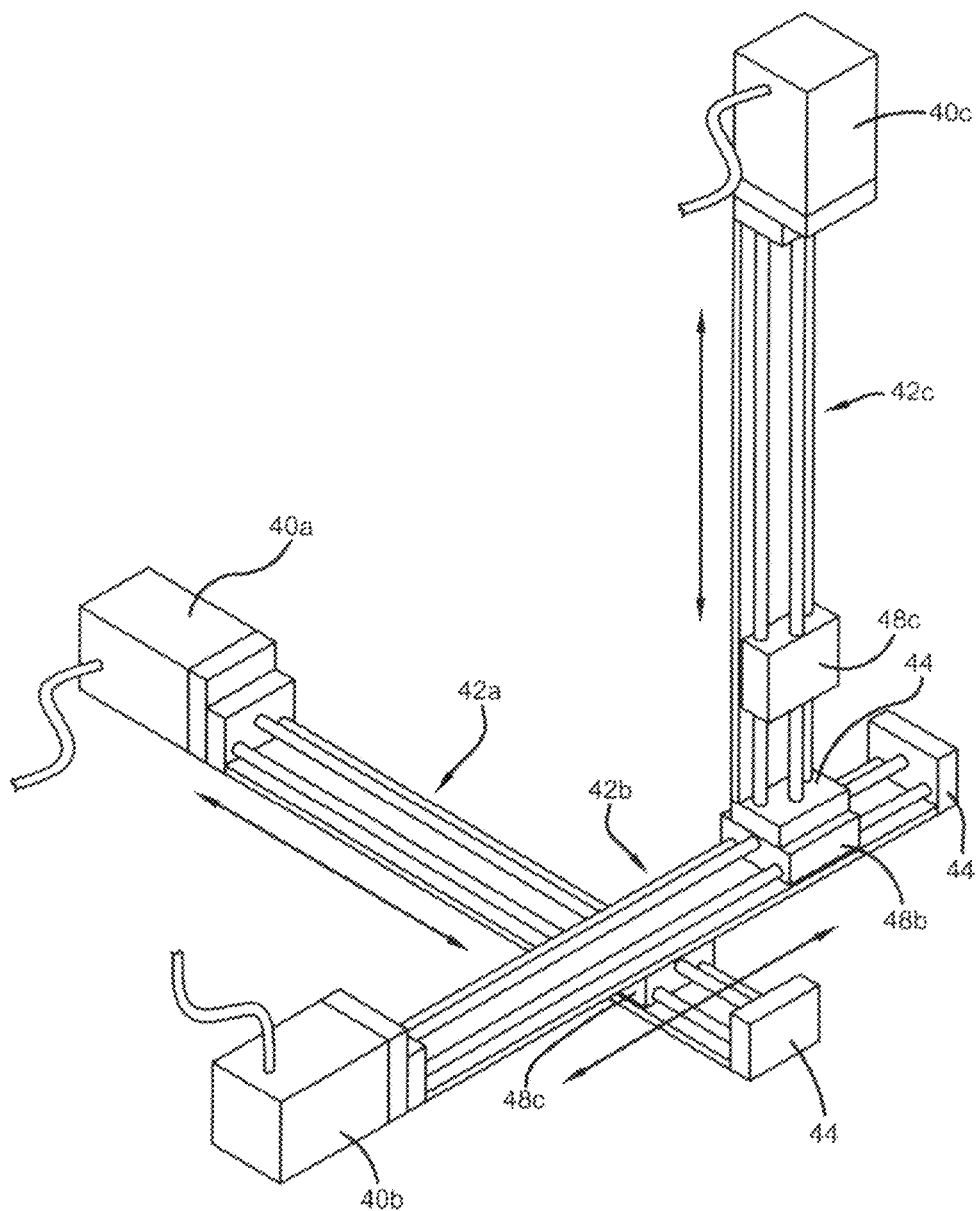
FIG. 4 is perspective view of a three dimensional motor and rail assembly according to at least one embodiment of the present invention.

The three dimensional bioprinter assembly 4 is best shown in FIGS. 2, 3 and 4. It includes a printing stage 10 configured to securely hold a container 12 having a printing surface 14, a printer head 16 having a printer cartridge 18 with one or more slots or openings 20 for securely holding one or more printing tips 22, and a three-axis motion control system 24 configured to move cartridge 18 in three dimensions with respect to the printing surface 14, and may be placed on and/or secured to a stabilizing platform 26. Printer head 16 is moved in three dimensions by three dimensional bioprinter assembly 4 and may or may not be considered part of the three dimensional bioprinter assembly 4. Stabilizing platform 26 provides a solid base for three dimensional printer assembly 4 to prevent or limit vibrations that would interfere with automated printing of cells in a spatially and temporally controlled manner.

As one of skill in the art will appreciate, stabilizing platform 26 may be any size or shape provided it can provide a solid base for three dimensional printer assembly 4, but it is preferably flat, level, and has a top surface 28 that is larger in area than the foot print of the three dimensional printer assembly 4. In some embodiments, stabilizing platform 26 is a metal plate having a top surface 28 at least 30% larger in area than the foot print of the three dimensional printer assembly 4. In some embodiments, stabilizing platform 26 is a metal plate having a top surface 28 at least 50% larger in area than the foot print of the three dimensional printer assembly 4. In some embodiments, stabilizing platform 26 is a metal plate between 6.35-(0.25 in) and 254 (10 in) mm thick. In some embodiments, stabilizing platform 26 is a large aluminum plate between 6.35 mm and 254 mm thick.

The printing stage 10 is the area and/or structure that supports the container 12 holding the printing surface 14 and should be of a suitable size and shape to accommodate container 12 and place it in position for printing. In some embodiments, printing stage 10 is designed to hold different sizes of commercially available culture plates. In some embodiments, printing stage 10 is located on the top surface 28 of stabilizing platform 26 and may be secured thereto by any means known in the art for that purpose including without limitation, screws, bolts, pins and fasteners, magnets, washers, anchors, nails, rivets, studs, welding, and/or soldering.

In some embodiments, printing stage 10 may be comprised of a first and second plate 30, 32. First plate 30 is secured to the top surface 28 of the stabilizing platform 26 and the second plate 32 is secured to the first plate 30 and directly or indirectly to container 12. The first plate 30 may be secured to the stabilizing platform 26 by any means known in the art for that purpose including without limitation, screws bolts, pins and fasteners, magnets, washers, anchors, nails, rivets, studs, welding, and/or soldering. In one embodiment, the first plate is secured to the stabilizing platform 26 by a plurality of socket cap, threaded machine, and/or thumb screws. The second plate 32 may be secured to the first plate 30 and directly or indirectly to container 12 by any means known in the art for that purpose including without limitation, screws, bolts, pins and fasteners. In one embodiment, the second plate 32 may be secured to the first plate 30 by a plurality of screws or bolts.

The container 12 holds the printing surface 14 and may be of any size or shape consistent with the size of the printing surface 10 and the proper operation of the three dimensional printer assembly 4. In some embodiments, the container may be a 60-mm polystyrene dish. Container 12 may be secured directly or indirectly to the printer stage 10 by any means known in the art for that purpose. In some embodiments, container 12 may be secured to the printer stage 10 by a plurality of brackets or fasteners. In some embodiments, container 12 may be secured to the stabilizing platform 26 or a table or workbench.

In some embodiments, container 12 may be secured to the printer stage 10 by means of a holder 34, which is secured to the top surface 36 of printer stage 10 and has a recessed area or aperture 38 configured to receive and secure the container 12. (See FIG. 5). Holder 34 may be made from any suitable material including without limitation plastic, metal, rubber, plexiglass, resin, metal, aluminum, or glass. Holder 34 may be secured to the top surface 36 of printer stage 10 by any means known in the art for that purpose including without limitation, screws, bolts, brackets, anchors, magnets, pins and fasteners. In some embodiments, holder 34 was made of a rectangular piece of Plexiglas containing a negative relief of a 60-mm polystyrene petri dish (FIG. 6C) In some embodiments, holder 34 may be designed in Solid-Works and fabricated using high-powered machining tools.

In some embodiments, printing surface 14 may be a cell monolayer or other biomaterial to which the cells may attach and grow. In some embodiments, printing surface 14 is a decellularized matrix. Decellularized matrices are biologically active surfaces that promote cell adhesion and growth and thus provide an appealing alternative to cell monolayer for printing with ATPS. In some embodiments, printing surface 14 may be a high-density matrix laid down by a 90-100% confluent layers of cells. Similar to a cell monolayer, a high-density matrix laid down by a 90-100% confluent layers of cells generate stable patterns of high-fidelity.

Turning now to FIGS. 3 and 4, the three dimensional printer assembly 4 further includes a three axis motor control system 24 having a set of three linear axis programmable stepping motors 40a, 40b, 40c that drive three motorized linear slides 42a, 42b, 42c positioned in horizontal (x) 42a, orthogonal directions (y) 42b, and vertical (z) 42c. In one or more embodiments, each of the motorized linear slides 42a, 42b, 42c are comprised of a motor 40, an end plate 44, one or more rails 46 and a carriage 48. Operation of motors 40 moves the carriage 48 in both a forward and a backward direction along the rails 46 of each one of the motorized linear slides 42a, 42b, 42c.

Figure 5:
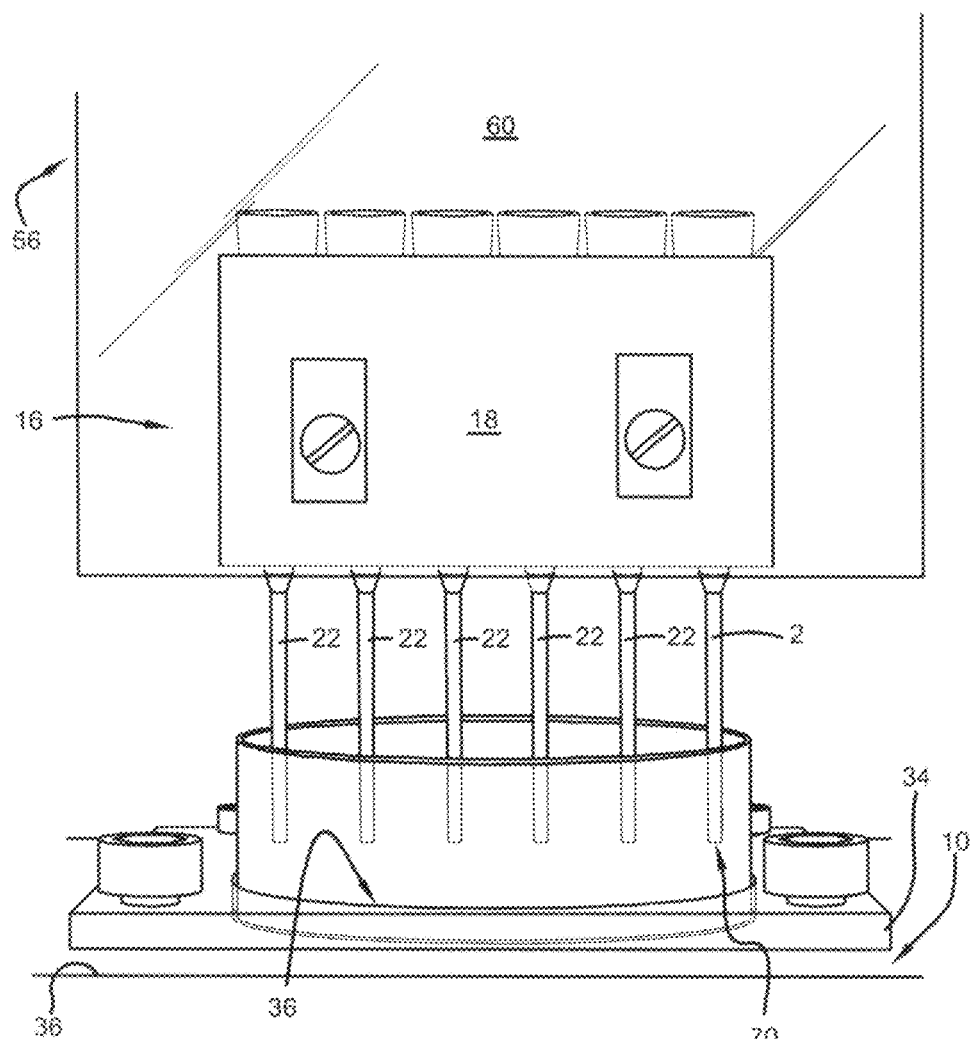
FIG. 5 is front view of a bioprinter head assembly according to at least one embodiment of the present invention.
Figure 6A:
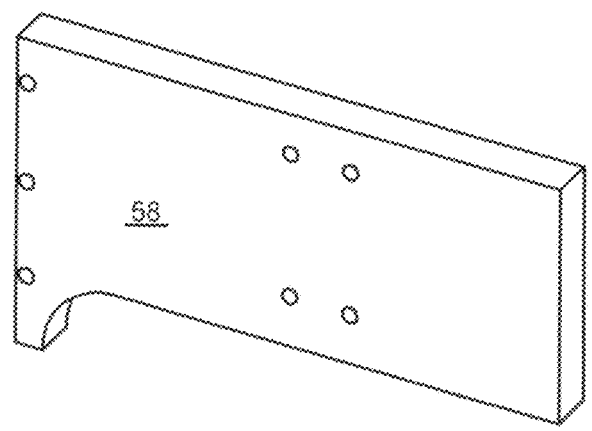
FIG. 6A-D are perspective views or: a first piece of the extension arm used to provide cartridge motion over the entire printing stage. (6A), a second piece of the extension arm used to house the printing cartridge (6B), a holder for 60-mm petri dish (6C), and a printing cassette designed to house printing tips (6D) according to at least one embodiment of the present invention.
Figure 6B:
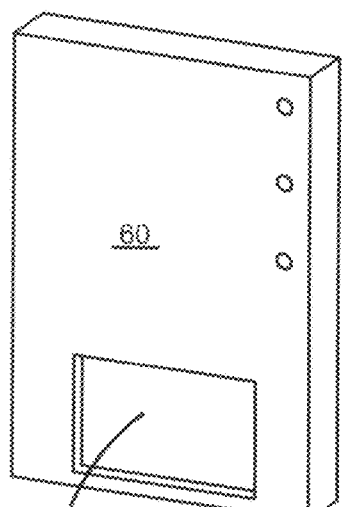
Figure 6C:
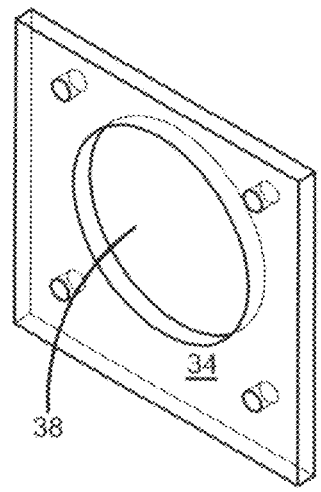
Figure 6D:
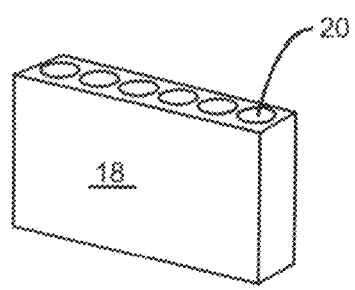

The linear slides 42a, 42b, 42c may be assembled in an XYZ configuration as shown in FIG. 5 using mounting cleats (not shown). To enable 3D motion capability without tilting of the system, one of the horizontally oriented slides (the slides in the x-direction 42a or y-direction 42b) may be cleated or otherwise secured to stabilizing platform 26, (See, FIG. 3). In some embodiments, the slide moving in the y-direction 42b is cleated or otherwise secured to the stabilizing platform 26 and the slide moving in the x-direction 42a is then secured to the carriage 48b of the slide moving in the y-direction 42b. In these embodiments, the slide moving in the z-direction 42c is then cleated or otherwise secured to the carriage 42a of the slide moving in the x-direction 42a, to permit movement in three dimensions. In some other embodiments, the slide moving in the x-direction 42a is the one cleated or otherwise secured to the stabilizing platform 26 and the slide moving in the y-direction 42b is then secured to the carriage 48a of the slide moving in the x-direction 42a. In these embodiments, the slide moving in the z-direction 42c is then cleated or otherwise secured to the carriage 48b of the slide moving in the y-direction 42b, to permit movement in three dimensions.

It should also be appreciated that the length of linear slides 42a, 42b, 42c and their travel distance will depend upon the size of the printing surface 14. In one embodiment, the printing surface was approximately the size of a 60-mm polystyrene dish and the two linear slides 42b, 42c coupled to the y-direction and z-direction motors 40b, 40c had travel distances of four inches (101.6 mm). To accommodate for a greater range of horizontal motion across the culture dish, the slide on the x-direction motor 42c was specified to have a travel distance of six inches (152.4 mm). In addition, the Z-axis linear slide had sufficient load capacity (10 lbs) to carry the added printing tools.

The linear axis programmable stepping motors 40a, 40b, 40c are not particularly limited and may be any electrical motor provided that enables automated backward and forward motion in a vertical and/or horizontal directions. In some embodiments, linear axis programmable stepping motors 40a, 40b, 40c are XSlide EO1, linear axis programmable stepping motors manufactured by Velmex (Bloomfield, N.Y.). In addition, the Z-axis linear slide 42c should possess a sufficient load capacity to carry the added printing tools.

In some embodiments, three dimensional printer assembly 4 further comprises an end cap 50 containing a roller ball bearing 52 mounted to the bottom end 54 of the Y-axis linear slide 42b, which provides extra support to the system and enables smooth horizontal positioning of the Y-axis linear slide 42b (FIG. 3).

Three dimensional printer assembly 4 further comprises a printer head 16 connected to the carriage 48b on z-axis linear slide 42c by extension arm 56. (See FIGS. 3, 5, and 6) Extension arm 56 extends from the z-axis linear slide and over the printing stage 10 to support motion of the printer head 16 across the printing stage 10. While it has been described and shown as attached to the z-axis linear slide 42c, it should be appreciated that this is because in these embodiments the z-axis linear slide is the only linear slide free to move in three dimensions. However, there are other configurations within the scope of the present invention where the x-axis linear slide 42a or y-axis linear slide 42b are the one that is free to move in three dimensions. In those configurations, the extension arm 56 would be secured to those linear slides.

Extension arm 56 may be made of any rigid material capable of supporting the weight of printer head 16 and which is not too heavy for the linear axis programmable stepping motors 40a, 40b, 40c to move. Suitable materials include, without limitation, aluminum, Plexiglas, stainless steel, any other metal, and/or plastic.

In some embodiments, extension arm 56 may be constructed from two or more parts. In some embodiments, extension arm 56 may be constructed of two separate pieces of Plexiglas. (See, FIGS. 6A, 6B). To avoid interference of this piece with the supporting stage during motion, a first piece 58 (FIG. 6A) extends out over the printing stage 10 and is secured to a second arm piece 60 (FIG. 6C), which holds printer head 16. In some embodiments, the second arm piece 60 may have a cut-out 62 in the shape of the printer head 16 to help hold it in place. Printer head 16 may be secured to extension arm 56 by any means known in the art for that purpose including without limitation, screws, bolts, brackets, pins, magnets, and fasteners. In some embodiments, a magnet may be placed at the rear of the printer head 16 to ensure easy and secure attachment of the printer head 16 to extension arm 56. FIGS. 3 and 5 show the entire assembly.

A printer head 16 according to one or more embodiments of the present invention is shown in FIG. 6 and may be comprised of a printer cartridge 18 configured to securely hold one or more printing tips 22. Printer cartridge 18 may be made from any rigid material capable of securely holding one or more printing tips 22 including without limitation, aluminum, plastic, rubber, metal, glass, Plexiglas, stainless steel, and polytetrafluoroethylene (PTFE). In some embodiments, cartridge 18 may be designed in SolidWorks and fabricated using high-powered machining tools. (See, FIG. 6D)

In some embodiments, printer cartridge 16 has one or more slots or apertures 20 cut into or through it for securing one or more printing tips 22. (See FIG. 5, 6D) In some embodiments, printer cartridge 16 has from 1 to 6 slots or apertures cut into or through it for securing one or more printing tips 22. In some embodiments, each tip slot 20 within the cartridge 18 was designed with several tapered sections matching the architecture of printing tips 22, to prevent movement or wiggling of the tip during mounting and printing, and inconsistent tip placement upon subsequent rounds of printing.

Figure 7A:
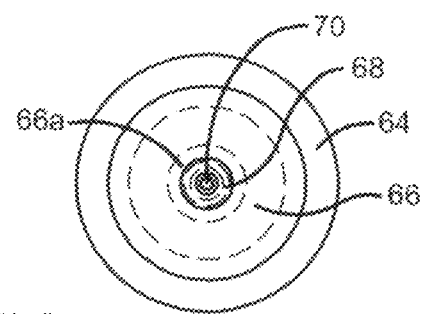
FIG. 7A-C are a top view (7A), front view (7B), and partial cross-sectional view of a printer tip according to at least one embodiment of the present invention.
Figure 7B:
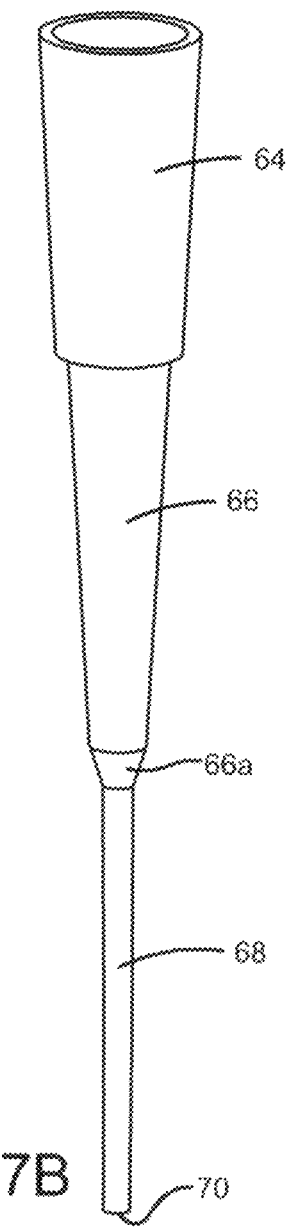
Figure 7C:
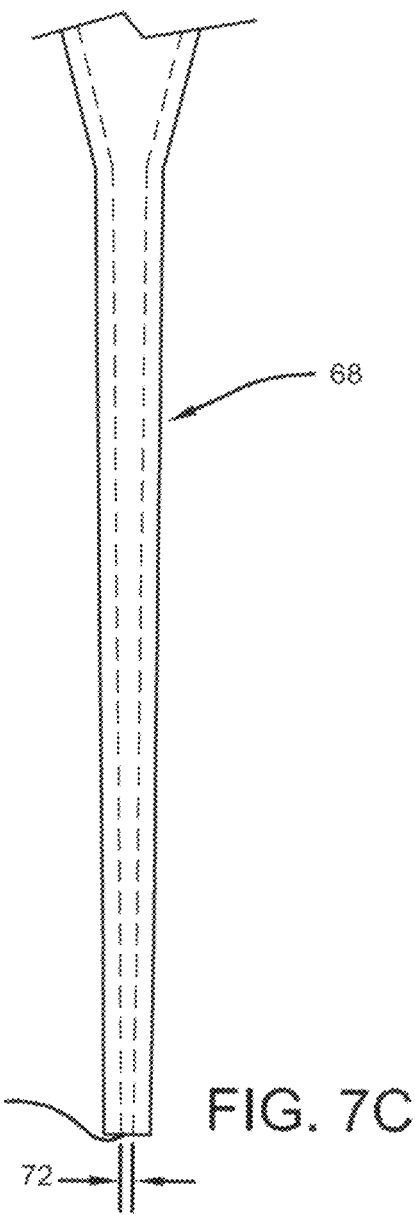

A printer tip 22 according to one or more embodiments of the present invention is shown in FIGS. 7A-C. In some embodiments, printer tip 22 has an upper reservoir section 64, a tapered section 66 having a neck portion 66a and an elongated end section 68. Prior to use, the cell containing printing solution is placed in the reservoir section 64 of the printing tip 22 and while some of the cell containing printing solution will fill the balance of the tip 22, most of it will remain in the reservoir section 64 where most of it stays until use. In some embodiments, only a relatively small volume of cell containing printing solution is used and the level of the cell containing printing solution in tip 22 does not reach the reservoir section 64 of the printing tip 22. In some of these embodiments, the level of the cell containing printing solution in tip 22 reaches only to the neck portion 66a of tapered section 66. While not particularly limited, printing tip 22 should be sufficiently rigid so that the elongated end section 68 does not move or wiggle during printing.

As the cell containing printing solution is dispensed, it moves from the reservoir section 64 through the tapered section 66 where the diameter is gently reduced until the cell containing printing solution reached the elongated end section 68 and exits the tip 22 through end opening 70. (See FIGS. 5, 7A-C). In some embodiments, end opening 70 has a diameter 72 of from about 200 μm to about 1300 μm. In some embodiments, the diameter 72 of end opening 70 is from about 200 μm to about 800 μm. In some embodiments, the diameter 72 of end opening 70 is from about 200 μm to about 600 μm. In some embodiments, the diameter 72 of end opening 70 is from about 200 μm to about 500 μm. In some embodiments, the diameter 72 of end opening 70 is from about 300 μm to about 500 μm. In some embodiments, the diameter 72 of end opening 70 is from about 300 μm to about 400 μm. In some embodiments, diameter 72 of end opening 70 is about 300 μm.

In addition, as the cell containing printing solution is, as set forth above, dispensed by gravity and as one of ordinary skill in the art would appreciate, the volume and therefore the weight of the column of cell containing printing solution brought to bear on end opening 70 will also affect the speed at which the cell containing printing solution is dispensed and, therefore, the printing resolution. (See Example 10, below) The appropriate loaded volume will, of course depend upon the size and configuration of the printing tips 22 being used as well as the printing speed and the desired printing resolution. If the loaded volume is too high the cell containing printing solution will come out too fast and the printing resolution will be poor. If the loaded volume is too small, the cell containing printing solution will be slow to dispense and the printed cell lines will show necking or break up into droplets. In some embodiments, the loaded volume may be from about 6 to about 36 μm. In some embodiments, the loaded volume may be from about 6 to about 14 µm. In some embodiments, the loaded volume may be from about 6 to about 12 µm. In some embodiments, the loaded volume may be about 8 µm.

Automated cell printer 2, further comprises at least one motor-controller 6 to provide the capabilities of manual and automated positioning of all three motors. The motors 40a, 40b, 40c on each linear slide 42a, 42b, 42c are electrically connected to at least one motor-controller 6 by the appropriate wires or cables (See, FIG. 2). The motor controllers 6 are not particularly limited and may be any motor controller appropriate for use with the motors 40a, 40b, 40c selected, provided that enables automated forward and backward motion in vertical and/or horizontal directions. If more than one motor controller are used, they may be linked by a bus cable (not shown) in order to provide simultaneous movement of all three motors. In one or more embodiments, two stepping motor-controllers with linked controls (bus cable) are used which provide the capabilities of manual and automated positioning of all three motors. In some embodiments, unipolar motor-controllers that feature an easy-to-use graphical user interface for programming are commercially available and may be purchased from Velmex, Inc. may be used.

Automated cell printer 2, further comprises computer 40. In some embodiments, the computer 40 uses a Microsoft Windows® Operating system. In some embodiments, interfacing the motor-controllers with a computer 8 was realized using a RS-232 converter. In some embodiments, computer-programming of motor-driven linear assemblies was realized through a user-friendly Computer Optimized Stepping Motor Operating System (COSMOS) software package that communicates to the motor-controllers via a serial port and provides temporal control and enhanced spatial control of positioning cells. COSMOS employs a command language made of ASCII (text) characters. The COSMOS software package features drivers for various programming languages such as LabVIEW and Matlab, but also features a the built-in programming language.

Since in these embodiments, each linear slide consisted of a stepping motor that moves in stepwise increments, the motor-controllers read in commands in "step" units. Each revolution of a stepping motor shaft consisted of 400 steps and equaled 1 inch. Accordingly, commands are passed to each motor indicating exact speed, forward or reverse direction, and travel distance. A command for speed, for example, may be entered as, $$SmMx, \quad [3]$$

where S signals a speed index to the motor-controller, m represents the motor-axis, and M signals to the motor an x, speed in steps/sec. In some embodiments, the motor-controllers may be limited to a speed range of 1-6000 steps/sec, or 0-15 in/sec (0-38.1 mm/sec). Similarly, a command for the travel distance may be entered as, $$ImMx \text{ or } ImM-x, \quad [4]$$

where I signals a distance index to the motor-controller, in either the clockwise or counterclockwise direction as indicated by the presence or absence of a hyphen between the M and x. The resolution of motion on each linear slide is 6.35 µm. Complex motion profiles are programmed using a Continuous Index Mode to enable smooth transitioning between motors. Having two motor-controllers also enables coordinated motion of multiple motors to produce angles, arcs, and circles. Multiple commands are compiled into a script and stored as a program for future use.

The program scripts for printing linear patterns and user-defined patterns such as the letters "UA" are shown in Appendixes A-C. Appendix A shows a sample code in Statistical Analysis System (SAS) written to perform a tukey t-test of statistical difference for pattern width corresponding to different tip inner diameters. Appendix B includes sample COSMOS codes for printing a linear pattern and the letters "UA," and Appendix C a matlab code for calculating the radii of curvature on a pattern exhibiting necking that resolves in droplets.

Prior to using the automated cell bioprinter 2 of the present invention, it may be necessary to calibrate the bioprinter prior to use. This process may include, without limitation, the following actions and measurements. First, the printer head 16 may be calibrated to the printing surface 14 to ensure that when the tips 22 are lowered into the container 12, the tips will be within a few hundred micrometers vicinity of the printing surface 14 without touching it. In some embodiments, the distance between the end opening 70 of the printing tip 22 and the printing surface 14 is from about 10 µm to about 5 mm. In some embodiments, the printer head 16 may be calibrated to the container 12, by manually jogging the Z-axis motor toward the dish until the printing tool touched a sample dish floor at which point it is then programmed to ascend to a programmed height plus <78 steps, or <500 µm. Second, the holder 34 was calibrated to container 12 to ensure that the container 12 is an exact, pre-defined orientation with respect to the holder 34. In some embodiments, a matching line may be etched on the holder 34 and container 12 using a fine scalpel and ruler. In some embodiments, the printing tips may also be calibrated to the cartridge to ensure that they are all at the same level with respect to the printing surface.

In another aspect, the present invention is directed to methods of printing cells using the above described automated cell bioprinter 2. In some embodiments, the method may comprise the following steps. First, preparing an aqueous cell containing medium containing a first aqueous polymer. See FIG. 8A and Example 1. In some of these embodiments, the first polymer is dextran. In some of these embodiments, the cells types may any cell type, provided that they are stored in the proper cell specific media. Suitable cell types may include, without limitation, MD-MBA 231 breast cancer cells, C2C12 mouse myoblast cells, mouse embryonic stem cells, rat endothelial cells, human umbilical vein endothelial cells (HUVECs), rat smooth muscle cells, neurons, PA6 stromal cells and combinations thereof.

Second, loading said aqueous cell containing medium into the one or more printing tips 22. It should be appreciated, however, that this step can take place at any point in the method prior to dispensing the aqueous cell containing medium onto the printing surface, as described below.

Third, preparing a second aqueous polymer solution (See FIG. 8B and Example 1), wherein said second aqueous polymer solution is less dense than and immiscible with said aqueous cell containing medium so that when the second aqueous polymer solution and aqueous cell containing medium are mixed a partition is formed there between with the aqueous polymer solution partitioned on the top and the aqueous cell containing medium.

Next, providing a cell monolayer or biomaterial surface upon which the cells are to be printed. In some embodiments, the cell monolayer or biomaterial surface may be a 95-100% confluent cell monolayer of any cell type, a decellularized matrix, or combinations thereof. In some embodiments, the cell monolayer or biomaterial surface may include previously printed cells. Although it need not be, the cell monolayer or biomaterial surface is ordinarily housed within a container, which is then secured to the printing stage 10 or stabilizing platform 26 of the automated cell bioprinter 2.

The cell monolayer or biomaterial surface is then covered with second aqueous polymer solution to a depth of from about 1 to about 15 mm. In some embodiments, the monolayer or biomaterial surface upon which the cells are to be printed is provided and covered with second aqueous polymer solution to a depth of from about 2 to about 10 mm. In some embodiments, monolayer or biomaterial surface upon which the cells are to be printed is provided and covered with second aqueous polymer solution to a depth of from about 4 to about 7 mm. In some embodiments, monolayer or biomaterial surface upon which the cells are to be printed is provided and covered with second aqueous polymer solution to a depth of about 5 mm. In some of these embodiments, the aqueous polymer solution contains polyethylene glycol (PEG).

In some of these embodiments, the interfacial tension between the second aqueous polymer solution and the aqueous cell containing medium is from about 10 to about 14 uN/m. In some of these embodiments, the interfacial tension between the second aqueous polymer solution and the aqueous cell containing medium is 12 μN/m. In some of these embodiments, partition coefficient between the second aqueous polymer solution and the aqueous cell containing medium is 0.78 or greater than 0.78. In some of these embodiments, partition coefficient between the second aqueous polymer solution and the aqueous cell containing medium is about 0.78.

Next, one or more printing tips are inserted into slots in the printing cartridge configured to receive said printing tips and lowered into the container containing the polymer phase to begin dispensing. It is believed that dispensing of the aqueous cell containing medium within the polymer phase takes place because the extremely small interfacial tension between the second aqueous polymer solution (PEG phase) and the aqueous cell containing medium (DEX phase) (about 12 uN/m) cannot hold the aqueous cell containing medium at the end opening 70 of the printing tip 22 against the force of gravity, causing it to autonomously dispense independent of any cell-damaging forces. Moreover, as shown below, the gravitation potential energy per unit area is significantly greater than the two-phase interfacial tension allowing it to thus pull the aqueous cell containing medium out of the dispensing tip and continuously dispense. It should be appreciated, however, that dispensing DOES NOT take place outside the second aqueous polymer solution (PEG phase), as there is no force acting to pull the aqueous cell containing medium out of the printing tip 22. Since cells are only about 5 μm in diameter, which is significantly smaller than the tip inner diameter, the cells are also dispensed. See FIG. 8C.

The three-axis motion control system has been pre-programmed to instruct the motors to move the printing cartridge in three dimensions and at a predetermined speed to place the printing tips at specific predetermined locations as the aqueous cell containing medium is dispensed onto the monolayer or biomaterial surface. The aqueous cell containing medium is then dispensed onto the cell monolayer or biomaterial surface as three-axis motion control system moves the printer head to the specific predetermined locations at a predetermined speed. In these embodiments, the cells are dispensed from said printing tips by the force of gravity, as set forth above.

In some embodiments, the method may also include allowing the cells in said aqueous cell containing medium to adhere to the cell monolayer or biomaterial surface and rinsing any un-adhered cells off said the monolayer or biomaterial surface. The cell monolayer or biomaterial surface and any cells adhered thereto with a layer of new layer of the second aqueous polymer solution and repeating the above steps to print a second layer of cells. In some embodiments, the steps may be repeated to produce a three dimensional array of cells. In some embodiments, more than one type of cells may be used.

Figure 9A:
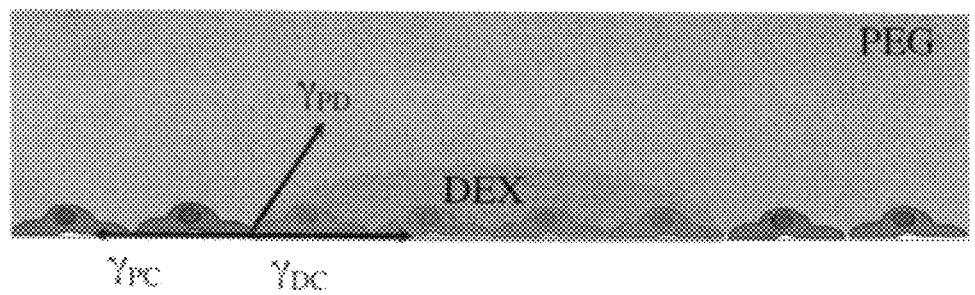
FIG. 9A-B.
Figure 9B:
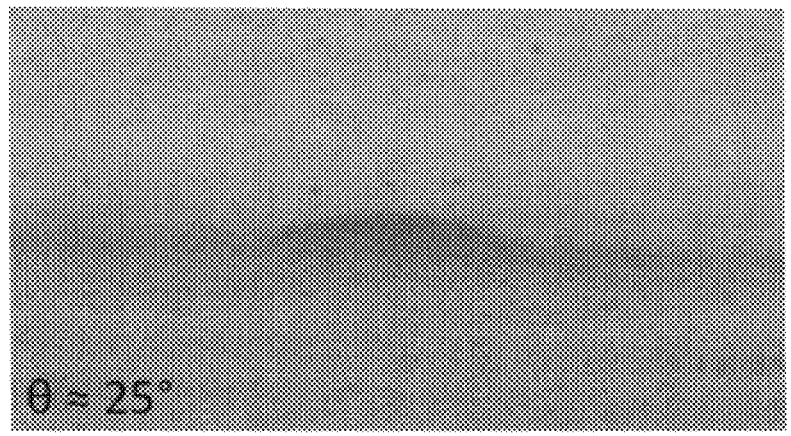

Intrinsically, the printing resolution will depend, at least in part, upon the interplay of gravity that tends to flatten printed patterns and net force of the three interfacial tensions at the three-phase contact point of the PEG-DEX-substrate shown in FIG. 9A, 9B. It should be appreciated that the balance of forces at the point of contact of the three phases of PEG-DEX-cell monolayer (FIG. 9A) will determine the final contact area, or pattern resolution. Gravity acting on the dispensing DEX phase, i.e., mgh, pulls it down to flattens it on the surface. It has been found that, other factors being equal, as the reagent height in the tip (and therefore its weight) increases, pattern width increases. (See FIG. 10A, 10*b*). Upon contacting the surface, a net force resulting from the balance between the three interfacial tensions, $\gamma_{PD}$, $\gamma_{PC}$ and $\gamma_{DC}$, is generated to resist and limit the spreading of the pattern to a completely thin film. To confirm this explanation, the potential energy due to the weight of the liquid column in the printing tip (See FIGS. 10A, 10B) was calculated based upon a density of 1000 kg/m3, a volume of 6 μl, and a height of 0.02713 m:

$$\rho: \text{density} \approx 1000 \frac{\text{kg}}{\text{m}^3}$$

$$v: \text{volume} = 6 \text{ μl} = 6 \times 10^{-9} \text{m}^3$$

$$g = 9.8 \frac{\text{m}}{\text{s}^2}$$

$$h = 26 + 1.3 \text{ mm} = 0.02713 \text{ m}$$

$$mgh = \rho \times v \times g \times h = 1.59 \times 10^{-6} \text{ J}$$

To compare this value with $\gamma_{PD}$ (0.012 mJ/m²), the gravitational energy per unit area may be calculated:

$$A_{tip\ orifice} = \frac{\pi}{4}(300 \times 10^{-6})^2 = 7.068 \times 10^{-8} m^2$$

$$\frac{mgh}{A_{tip\ orifice}} = 22569.9 \frac{\text{mJ}}{\text{m}^2}$$

The potential energy value is significantly greater than $\gamma_{PD}$ allowing gravity to pull the DEX phase out of the dispensing tip to continuously dispense.

It has been found that the resolution of printed patterns can also be controlled by several tunable design parameters including linear printing tip speed, loaded volume of printing phase in the tip, printing tip dimensions and the printing surface.

As set forth above, the newly developed automated cell bioprinter enables spatial and temporal control over positioning of cells on biological surfaces and can print non-circular patterns with resolutions as fine as 322±64.5 μm. To explain pattern instability, images of unstable patterns were analyzed at the point of breaking to show that breakage occurs due to the presence of different curvatures along the patterns that give rise to large capillary pressures. (See FIG. 11A, 11B)

As will be appreciated, pattern width and stability may also be dependent on the linear speed of the printing tips 22. As the linear speed in increased there may be seen a corresponding decrease in pattern width until the pattern becomes unstable. See FIGS. 12A, 12B. Pattern resolution may also vary with the diameter 72 of the end opening 70 of the printing tip 22. See FIGS. 7A-C, 13.

In addition, it has been found that interactions between the printed DEX phase and biomolecules on the surface are crucial to maintaining stable patterns. To demonstrate the utility of this approach for spatially-temporally controlled cell printing, duplex patterns of cells were generated in multiple configurations. (See FIGS. 14A-H) To show capabilities of printing complex geometries user-defined shapes 'UA' and 'NEOMED' were printed. (See FIGS. 15A-E)

Automated cell bioprinter 2 provides an automated platform to employ ATPS-mediated printing to (i) achieve greater spatial and temporal control over cell positioning, (ii) investigate pattern stability and fidelity, (iii) create heterocellular niches in multiple configurations, and (iv) generate user-defined cellular patterns. Unlike the few existing cell printing approaches that use external mechanical, thermal, electrical, or fluidic forces to eject cells from a nozzle, printing with ATPS is autonomous without a need for forces that compromise viability of printed cells.

Potential uses of the autonomous cell bioprinter of the present invention are extensive and include, without limitation: (i) creating differentiation niches for embryonic stem cells by printing stem cells on a layer of supporting stromal cells. For example, embryonic stem cells printed on stromal PA6 skull bone marrow cells differentiate to cells of the neural system; (ii) creating organized cell constructs consisting of multiple cell types (the autonomous cell bioprinter can, for example, be used to create organized multi-layered muscle tissue where each layer of the construct consists mainly of myoblast cells and endothelial cells and rotates at a certain angle from the previous layer); and (iii) creating other tissues where cellular organization is important such as liver and kidney.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

Preparation of Aqueous PEG and DEX Stock Solutions

Figures 8A, 8B:
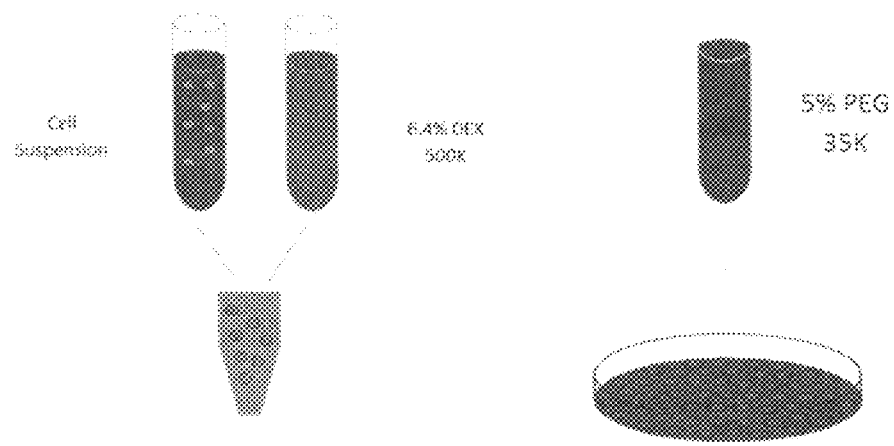
FIGS. 8A-C.
Figure 8C:
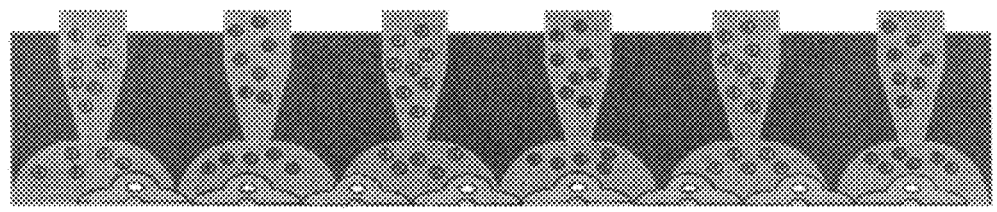

For all printing experiments, an ATPS with 5.0% (w/w) polyethylene glycol (PEG, Mw: 35 k) and 6.4% (w/w) dextran (DEX, Mw: 500 k), was used as phase-forming polymers. PEG and DEX were obtained from Sigma and Pharmacosmos, respectively. Each phase was individually prepared with these concentrations in growth medium. The DEX phase was prepared twice the final concentration to account for mixing with the PEG and cell suspension at a 1:1 ratio (FIG. 8A). Centrifuge tubes containing the solutions were allowed to rest in a vertical position at room temperature for ~2 hours for the polymer to fully dissolve. The stock solutions were then stored at 4° C.

Example 2

Preparation of Printing Surface and Printing Phase

For each experiment, the printing surface was maintained in 5% (w/w) PEG (FIG. 8B). Five different types of surfaces were prepared or provided to assess the stability of printed patterns of the DEX phase, including decellularized matrices, cell monolayer replica, live cell monolayers of different confluence, molecularly smooth films of poly(D,L-lactic acid) (PDLA), and PDLA with fabricated striped microgrooves of 10 and 20 μm pitch.

Preparation of each surface is briefly discussed: (i) Decellularized matrices of MDA-MB-231 breast cancer cells and C2C12 mouse myoblast cells were prepared by treating a confluent monolayer with a 0.25% (v/v) Triton X-100 (Sigma) solution in PBS for 15 minutes. The monolayer was then washed three times with PBS to ensure the complete removal of all cell constituents except for the protein matrix laid down by cells on the surface. When prepared at least a day before printing, samples were maintained in PBS and stored at 4° C. until use.

(ii) To create cell monolayer mold replicas with negative and positive indentations, cells were first fixed in a −20° C. methanol solution for 5 min and washed with PBS three times. A 10:1 mixture of polydimethyl siloxane (PDMS) and a curing agent (Sylgard 184, Dow Corning) was prepared, degassed under a vacuum desiccator until all bubbles disappeared, poured on fixed cells, degassed again, and baked in a 65° C. oven overnight. The cured PDMS was cut out with a surgical blade and transferred to an empty 60-mm petri dish to serve as the mold with negative indentations. To create a mold with positive indentations (i.e., same morphology as the cell monolayer), the PDMS mold containing negative indentations was placed in a vacuum chamber and treated with silane for ~2 hours, then covered with a layer of PDMS, degassed, and baked overnight at 65° C. Then the two PDMS slabs were carefully separated. The top layer, possessing positive indentations was used as the substrate for printing. To render it hydrophilic, the surface was exposed to oxygen plasma at 200 mTorr for 30 sec.

(iii) Cell monolayers of various confluence were prepared by adjusting seeding cell density to achieve 50, 75, and 100% confluence for printing.

(iv) Films of PDLA were prepared in three conditions; plain surface, and striped microgrooves of 10 and 20 μm pitch. Using the method reported in Yangjun, C; Newby, B. Z., "Fracture induced formation of parallel silicone strips." J. Mater. Res. 2010, 25, 803-809, the disclosure of which is hereby incorporated by reference in its entirety, first a 10:1 mixture of cured PDMS was prepared, oxidized for 15 minutes, and covalently bonded to a glass slide. The PDMS sheet was then separated from the glass slide using tweezers and weight (i.e., at a known peel force). The amount of weight applied when peeling determined the pitch of the strips.

Unless otherwise set forth herein, the printing phase for all experiments consisted of a 6.4% (w/w) DEX solution containing small traces of diluted fluorescein isothyiocyanate-dextran 500 k conjugate (FITC-DEX). The FITC-DEX dilution was prepared in de-ionized water (1.25 mg/ml), until its concentration was reduced to 5% of the original stock. The resulting solution was then mixed with the non-fluorescent DEX phase to facilitate fluorescent imaging. All printings tips were loaded with 8 µl of the printing phase and then programmed to descend into the PEG-covered surface for studies conducted to investigate the printing tip speed, tip inner diameter, and surface type. To study the effect of loaded volume in the tips, the amount of loaded DEX above the capillary column of the tips was imaged using a light microscope and measured. For cell printing experiments, the printing phase consisted of a 1:1 (v/v) ratio of 12.8% (w/w) DEX (non-fluorescent) and cell suspension. Cells were grown until 90-100% confluent, washed with PBS, trypsinized, centrifuged down, and counted on a hemacytometer. For imaging purposes, cells were first stained with a 2 µM calcein-AM solution for 30 min prior to printing. To generate linear patterns containing a dense population of cells, the cell suspension was centrifuged a second time and cells resuspended in an appropriate volume of media to result in a density of $12 \times 10^6$ cells/ml after mixing 1:1 with the 12.8% DEX phase solution. This suspension was thoroughly mixed prior to each successive round of printing to prevent cells from accumulating at the bottom of the centrifuge tube.

Example 3

Calibrations of the Three-Axis Motorized System

The three-axis motorized system was calibrated at the beginning of each experiment. The printer head containing the cartridge and printing tips was programmed to descend into an empty dish until the tip touched the dish surface. The printer head was then programmed to ascend ~500 µm (78 steps) to prevent tips from scraping the printed surface during printing. Another script of commands was developed to print individual patterns for characterization studies. The printing tips were programmed to descend into the dish (FIG. 8C), perform a linear forward motion, ascend out of the dish, and then move an offset distance to prepare for the next print. The offset distances between each printed line for co-culture cell printing experiments were determined based on measurements of line width from characterization studies with FITC-DEX printing.

Example 4

Design and Fabrication of Printing Tips

Figure 16A:
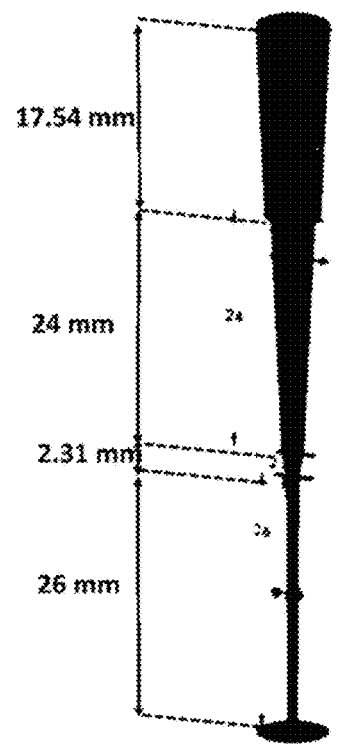
FIG. 16A-B are a front view (16A) and a top view (16B) of a printing tip according to at least one embodiment of the present invention providing dimensions.
Figure 16B:
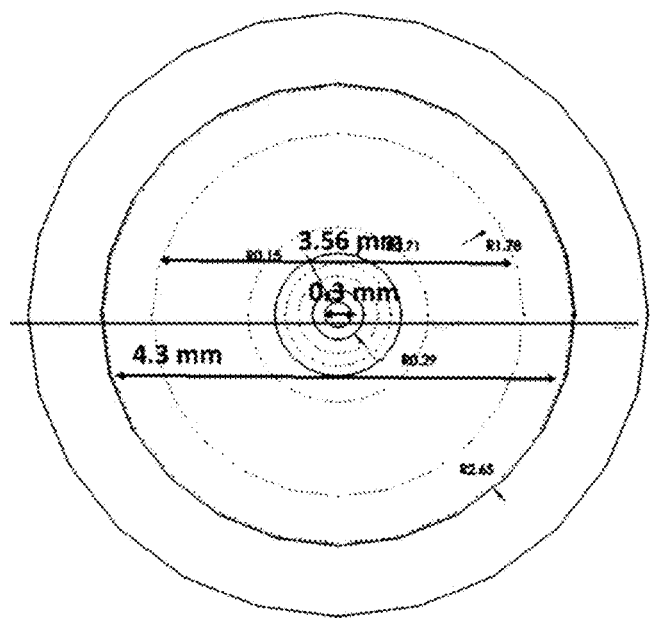

To study the effect of cross-sectional diameter of printing tips on printed patterns resolution, tips with four inner diameters of 200, 300, 575, and 750 µm were used. Tips of 200 µm were fabricated using a crude extrusion method. The new tips were designed to match the contour with the exact dimensions as gel-loading tips in other studies in this project that diameters of 300 µm. To make sure the tips have with the same geometry and dimensions as the gel-loading pipette tips, designs were created after carefully inspecting and accurately measuring dimensions of gel-loading tips under a microscope (FIG. 7A-C). Designs were submitted to a stereolithography rapid prototyping center for fabrication. Due to limitations in precision with the stereolithography tool, only two of the six designed tips could be fabricated according to our specifications. Both of these tips had larger diameters than gel-loading tips, i.e., 575 µm and 750 µm. To use tips with diameters smaller than 300 µm, a gel-loading tip was placed over a hot plate to soften and forceps used to pull the elongated end. The extruded tips were then placed onto a cutting board, carefully sliced above the original tip end point in the extruded region, and imaged under a microscope for inner diameter measurements. This extrusion process yielded tips with a diameter of 213.7 µm (rounded to 200 µm for this study). All sample tips were used to print linear patterns of FITC-DEX at speeds of 5-22 mm/s. FIGS. 16A and 16B show the dimensions of the printing tip used for these experiments.

Example 5

Creating Heterocellular Niches in Multiple Configurations

To create heterocellular niches or duplex prints in multiple configurations, 300 µm tips were loaded with 8.0 µl of the DEX phase containing green fluorescing cells and placed in the cartridge. Linear patterns of green cells were individually printed at a speed of 22 mm/s on the surface covered with the PEG phase. After each individual pattern was printed, registered coordinates of the x-axis stepping motor were manually recorded to know the coordinates for printing subsequent patterns of a different color. Once all green-cell patterns were printed, the printer head was programmed to return to its origin point of coordinates and the printed surface was placed in a cell culture incubator for 1 hr to allow cells to attach. Then ATPS media was replaced with complete growth media and cells were returned to the incubator for another 3 hrs to spread. The culture dish was loaded with the PEG phase again and placed back on the printing stage for printing red cells. Next, printing tips were loaded with red fluorescing cells and placed in the cartridge. The printer head was offset twice the distance (400 µm) of previously measured pattern widths at 22 mm/s from characterization experiments and linear patterns of the red cells were printed. For duplex cell printing in orthogonal and acute geometries, the dish was rotated at a forty-five degree and a ninety degree angle with respect to the stage prior to the second printing step.

Example 6

Creating User-Defined Shapes

Figure 15A:
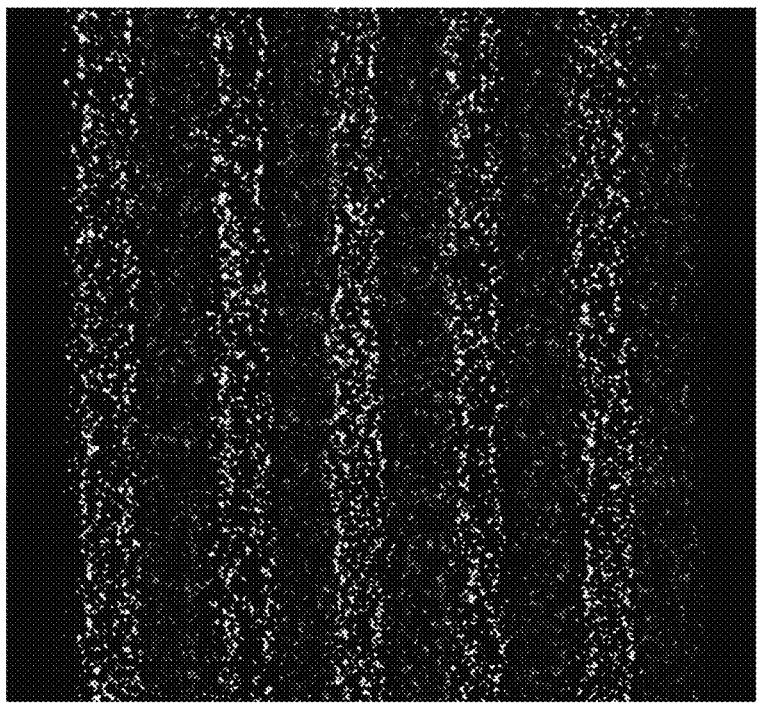
FIGS. 15A-E are a series of images showing cells duplex printed co-cultures on a cell monolayer in (FIG. 15A) parallel, (FIG. 15B) orthogonal, and (FIG. 15C) acute angle configurations.
Figure 15B:
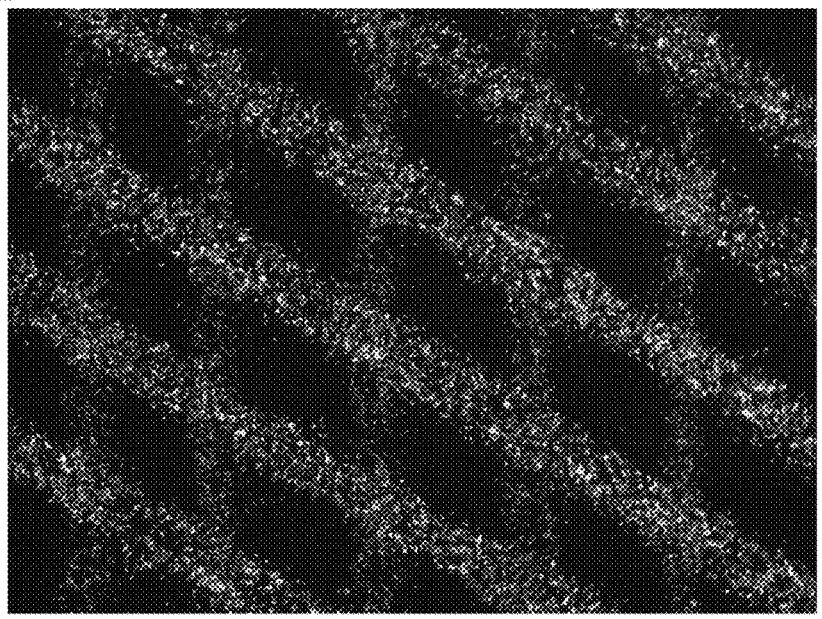
Figure 15C:
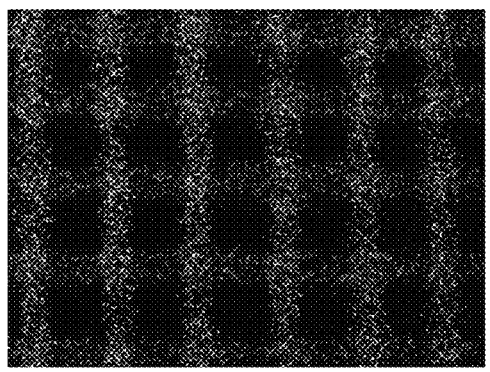
Figure 15D:
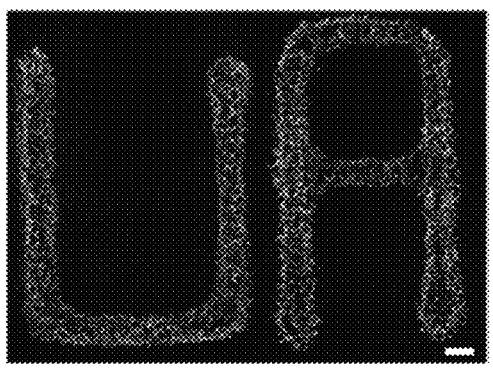

Patterns in the shapes, "UA," (standing for the University of Akron) and, "NEOMED," (standing for Northeast Ohio Medical University) were printed by continuous dispensing of C2C12 cells suspended in the DEX phase from an extruded pipette tip (inner diameter ~200 µm). The pattern, "UA," was printed in three separate steps (FIG. 15D). First, the letter U was printed with a loaded volume of 10 µl at a speed of 3.2 mm/s. Second, the x-axis motor was programmed to offset 1 mm to the right of the U, and the y-axis motor forward by the programmed side-length of the U, 7.4 mm. Then, the same tip was emptied of its contents and reloaded with 10 µl of the same printing phase, and a backward U was printed. For printing the middle line feature in the, the y-axis motor was programmed to move backwards half the height of the backward U, the tip reloaded with a volume of 5.25 µl, and a line connecting both ends of the backward U was printed to result in the shape, "A".

Similarly, the pattern, "NEOMED," was printed in eight separate steps, where only the letter, "E," required more than one step. Letters N, O, M, and D were printed with a loaded volume of 8 μl at a speed of 6.3 mm/s. The continuous index feature on the computer program enabled smooth motor-transition to print the diagonal sections in the shapes, N and M. Letter E was printed in two separate steps. First, the three outside line features were printed in one continuous stroke with a loaded volume of 8 μl at a speed of 6.3 mm/s. The middle line feature was then printed with a loaded volume of 5.25 μl at a speed of 6.3 mm/s. After all shapes were printed, the dish was incubated for 1 hour, after which the two-phase media was replaced with regular culture media, and the dish was returned to the incubator for 3 hrs. Then, printed patterns were imaged under a microscope to measure pattern resolution.

Example 7

Image Analysis and Measurements

After patterns were printed as set forth in Example 6, above and confirmed to be stable in ~5 min, the Petri dish was placed under a light microscope for imaging. To determine the width of the printed patterns, fluorescent images of FITC-DEX patterns were captured along several sections of the pattern at a magnification of 1.63× and analyzed using AxioVision software (Zeiss). Because printed lines of the DEX-containing aqueous phase exhibit jagged edges along their column due to hinging of the DEX phase on the cells of the surface, the area of the pattern was measured in AxioVision. An average line width was then calculated by dividing the calculated area by the vertical length of the image, as provided by the image scale. The results are shown in FIG. 12

Example 8

Analysis of the Effect of Printing Speed on the Resolution and/or Width of the Printed Patterns As described herein, a system has been designed that provides a user with an interface to program tunable speed for the printing tips in the X, Y, and Z directions. To perform printing of a simple linear pattern, tips containing cell suspension in the DEX phase were brought over the dish using the Y-axis and X-axis motors, lowered into the dish containing the PEG phase using the Z-axis motor, moved laterally with a pre-defined travel distance across the dish using the Y-axis motor, and then moved out of dish back to a next position to prepare for the subsequent printing step. The width of each linear pattern was found to depend on the speed of the Y-axis motor, and hence the speed of the printing tip, as it swept across the dish. The Z-axis motor, responsible for lowering the tips, was programmed to descend with a low speed (1.6 mm/s). A slow insertion speed of the tip is necessary since each tip is tapered with a long and thin capillary column at its end (FIG. 7) resulting in a slight delay of about ~1 second before dispensing. The Y-axis motor was programmed to sweep the dispensing tips across the dish at a user-defined speed. It is this speed that affected the resolution, or width, of printed patterns.

Figure 12A:
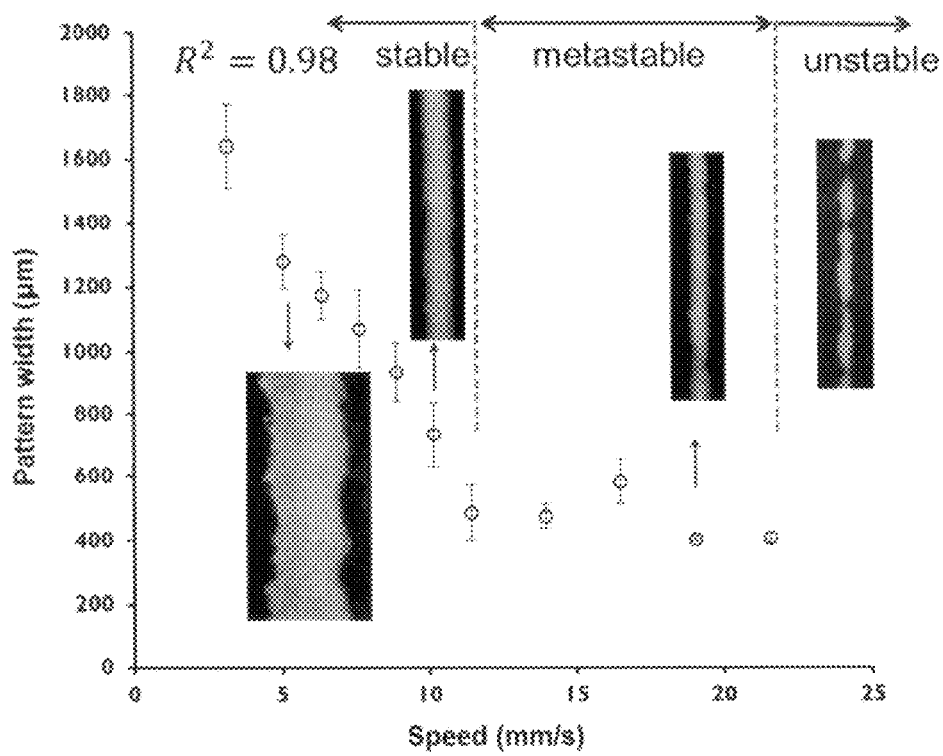
FIG. 12A-B.
Figure 12B:
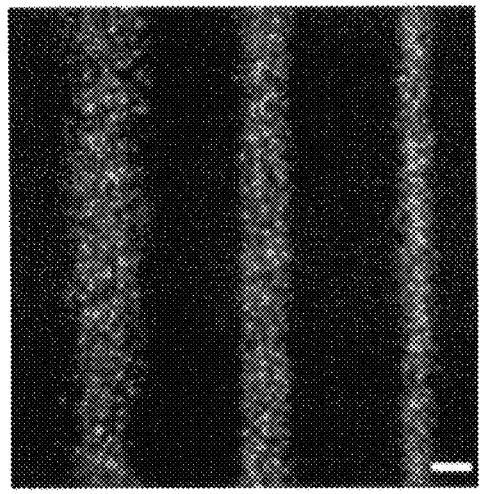
Figure 13:
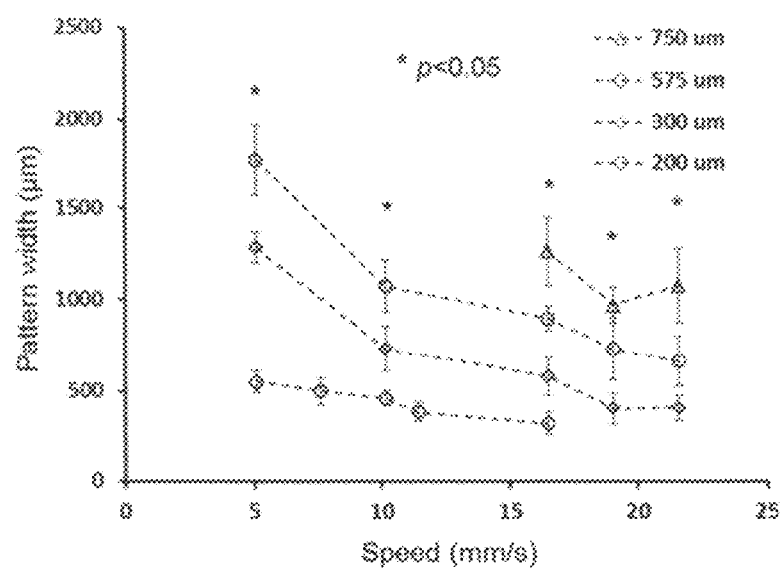
FIG. 13 is a graph showing how the resolution of printed patterns varies with the inner diameter of the pipette tip within the range of 200-750 µm. The asterisks indicate data from different tip diameters at the same speed are statistically different ($p<0.05$).

To capture the effect of lateral speed of dispensing tips on print resolution, individual linear patterns of FITC-DEX were printed through a single printing stroke, across a wide range of speeds of 3-22 mm/s. Experiments at each speed included a minimum of five replicates. All experiments were conducted with tips of 300 μm inner diameter, which were loaded with a volume of 8 μl. The results from these experiments are shown in FIG. 12A and can be divided into three regimes. In regime I, the lateral dimensions of the printed patterns directly depended on the DEX volume dispensed over a unit area of the surface swept by printing tips ($R^2=0.98$). As the tip speed increased within 3-12 mm/s, the size of patterns decreased laterally due to less spreading on the surface. The smallest pattern size is 487.5±86.2 μm. Since cells are always maintained in the DEX phase, this relationship between speed and pattern width was also observed in cell patterns (FIG. 12B), and therefore this principle can be applied towards cell printing. In regime II, increasing the tip speed up to 22 mm/s did not produce narrower lines anymore; here the width of printed lines remained more or less constant at 487.9±50.0 μm. Further increase in the printing tip speed beyond those tested in regime II resulted in unstable lines that showed necking along the patterns and broke into droplets (regime III). In this regime, the printed lines were initially 408.1±16.8 μm, but immediately pinched off at several locations.

In all three regimes, the balance of forces at the point of contact of the three phases of PEG-DEX-cell monolayer (FIG. 9A 5.2a) determined the final contact area, or pattern resolution. Gravity acting on the dispensing DEX phase, i.e., mgh, pulled it down to flatten it on the surface. Upon contacting the surface, a net force resulting from the balance between the three interfacial tensions, $\gamma_{PD}$, $\gamma_{PC}$ and $\gamma_{DC}$, was generated to resist and limit the spreading of the pattern to a completely thin film. To confirm this explanation, the potential energy due to the weight of the liquid column in the printing tip was calculated:

$$\rho: \text{density} \approx 1000 \frac{\text{kg}}{\text{m}^3}$$

$$v: \text{volume} = 6 \text{ μl} = 6 \times 10^{-9} \text{m}^3$$

$$g = 9.8 \frac{\text{m}}{\text{s}^2}$$

$$h = 26 + 1.3 \text{ mm} = 0.02713 \text{ m}$$

$$mgh = \rho \times v \times g \times h = 1.59 \times 10^{-6} \text{ J}$$

To compare this value with $\gamma_{PD}$ (0.012 mJ/m$^2$), the gravitational energy per unit area was calculated:

$$A_{tip\ orifice} = \frac{\pi}{4}(300 \times 10^{-6})^2 = 7.068 \times 10^{-8} \text{ m}^2$$

$$\frac{mgh}{A_{tip\ orifice}} = 22569.9 \frac{\text{mJ}}{\text{m}^2}$$

The potential energy value was significantly greater than $\gamma_{PD}$ allowing gravity to pull the DEX phase out of the dispensing tip to continuously dispense.

To determine pattern thickness of the experimental prints used herein, a cell monolayer was cultured on a thin glass slide. The slide was then placed on the bottom of a cuvette and immersed in the PEG phase. A sessile drop of the DEX phase was formed on a monolayer of C2C12 cells immersed in the PEG phase. Sideview images were taken (FIG. 9B) and the drop thickness and contact angle were measured. Measurements showed a 39.2 μm thickness at the drop apex with a contact angle of 25° (FIG. 9B). The small thickness and the low contact angle was due to an ultralow interfacial tension $\gamma_{PD}$=12 µN/m, and indicated why patterns less than a few hundred microns in width may not be achievable with ATPS microprinting.

In regime II, the pattern width was independent of the tip speed at higher speeds despite smaller dispensed volumes. At higher speeds, the interfacial tension $\gamma_{PD}$ (through its horizontal component), would tend to reduce the pattern width to compensate for smaller dispensed volumes. However this force was not large enough to overcome the net force $|\gamma_{PC}-\gamma_{DC}|$ that acts to pin down the pattern on the cell layer. As a result, patterns in this regime of speeds are referred to as energetically metastable for the fact they are not in their lowest energy state and can break if sufficient energy is provided, i.e., through vibrations. Finally in regime III (above 22 mm/s of printing tip speed), the dispensed volume was too small to counteract local pressure gradients along the three-phase interface of patterns that arise due to large local curvatures. As a result, patterns became hydrodynamically unstable, pinched off at several locations, and resulted in individual drops.

Figure 11A:
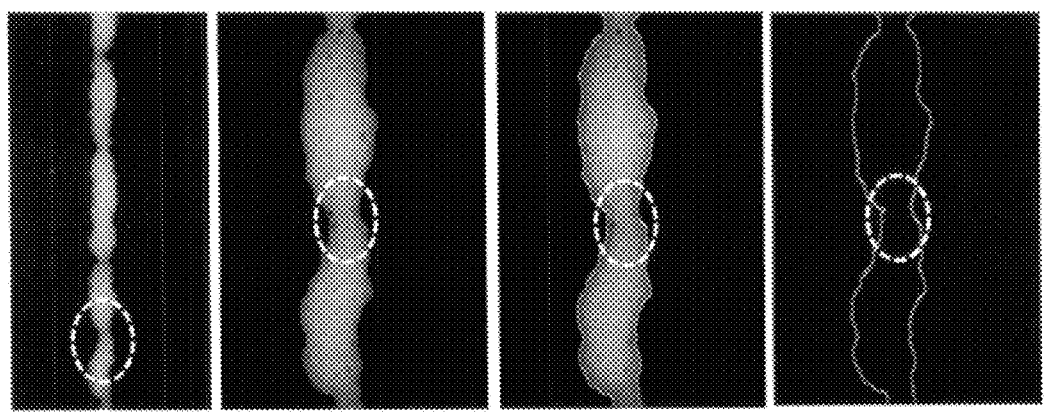
FIG. 11A-B.
Figure 11B:
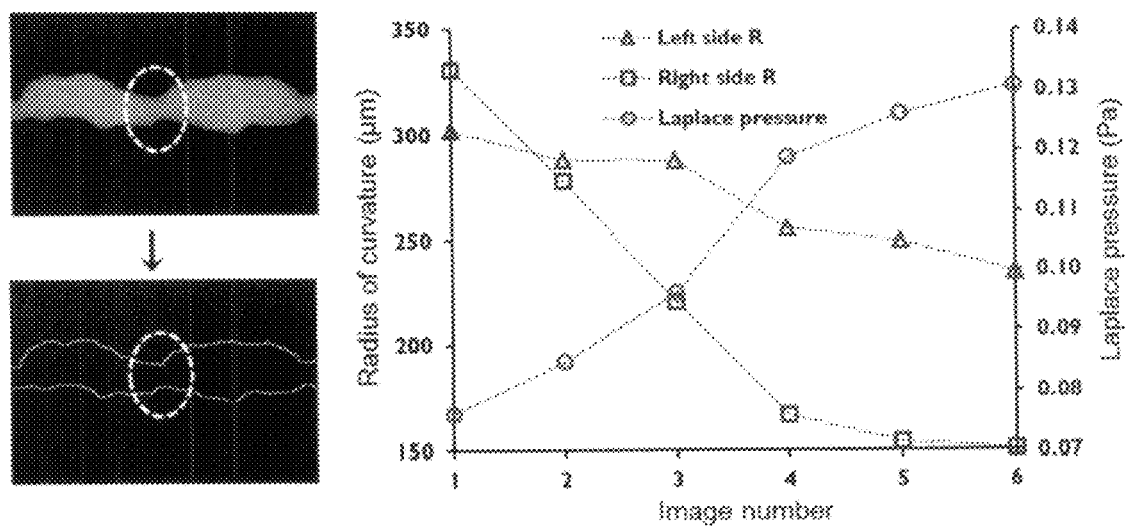

The breakage is initiated by curvatures of different radii along the interface of the PEG-DEX-cell layer and therefore differential capillary pressures. The printed phase (DEX) is a liquid inside the body of another liquid (the PEG immersion phase) and tends to be in a minimal energy state. Thus, when the net force $|\gamma_{PC}-\gamma_{DC}|$, could no longer resist the capillary pressure imposed by the differential curvatures along the DEX phase pattern, liquid drained from pinched areas of higher pressure (larger curvature) to bulging areas of lower pressure (smaller curvature) along the pattern column and created local necking that resulted in the breaking of the pattern into droplets (FIG. 11A, 11B). This phenomena, which resembles Plateau-Rayleigh instability, limited patterns to lateral sizes of 405.1±7.4 µm, and is theoretically applicable to other aqueous biphasic systems having an interfacial tension of 12 µN/m.

Example 9

Evaluation of Pattern Instability at High Printing Speeds

To explain pattern instability, an experiment was conducted to print patterns at high speeds (>22 mm/s) on a confluent cell layer. To rule out any possibility that external forces from vibrations in the PEG phase induce breakage, an LED lamp was shined on patterns immediately after printing. Patterns were observed to immediately begin changing shape after dispensing. Time-lapse images of an unstable pattern were captured to analyze the dynamic changes in the curvatures along the pattern. A total of sixteen images were captured and six were selected for quantitative analysis. Using the image processing toolbox in MATLAB software package, edges on the two sides along the pattern were extracted, and radii of curvatures on both ends were measured (FIG. 11A). Laplace pressures at the site of necking were calculated from the Laplace equation of capillarity to determine the evolution of capillary pressure in the course of necking until breakage:

$$\Delta P = \gamma_{PD}\left(\frac{1}{R_1} + \frac{1}{R_2}\right), \quad [5]$$

where $\gamma_{12}$ represents the interfacial tension between the PEG and DEX phases, and $R_1$ and $R_2$, are the measured radii of curvature values at the site of necking (FIG. 11B). From FIG. 11B, radii of curvatures shrunk with respect to time and breakage occurred as capillary pressures increased until liquid drains from the pinched area with a Laplace pressure of 130 mPa and radii of curvature of 220 µm to a bulging area with a radii of curvature of 150 µm.

Example 10

Effect of Loaded Volume on Pattern Stability and Resolution

In addition to increasing the speed of the printer head carrying the tips, experimental studies showed the amount of volume of printing phase loaded into printing tips also affected patterns width. To systematically capture this effect, tips were loaded with 6-8 µl of FITC-DEX at increments of 0.5 µl and linear patterns printed a single programmed speed of 1200 steps/s (7.6 mm/s) onto a confluent monolayer of C2C12 cells. A minimum volume of 5 µl was needed to fill the tip just above the capillary portion and initiate autonomous dispensing within seconds of tip insertion in the PEG phase. Tips loaded with smaller volumes can autonomously dispense from the tip but often requires the tip to remain stationary in the PEG phase for over a minute to allow enough DEX mass from inside the tip to overcome the interfacial tension, $\gamma_{PD}$, at the dispensing end of the tip. In addition, printing with loaded volumes below 6 µl resulted in patterns that broke into droplets similar to those in regime III of FIG. 12A.

Figure 10A:
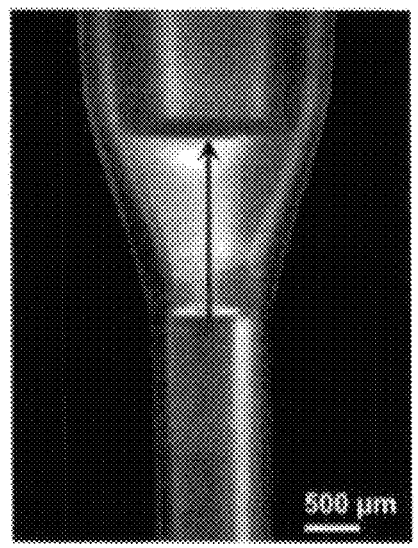
FIG. 10A-B.
Figure 10B:
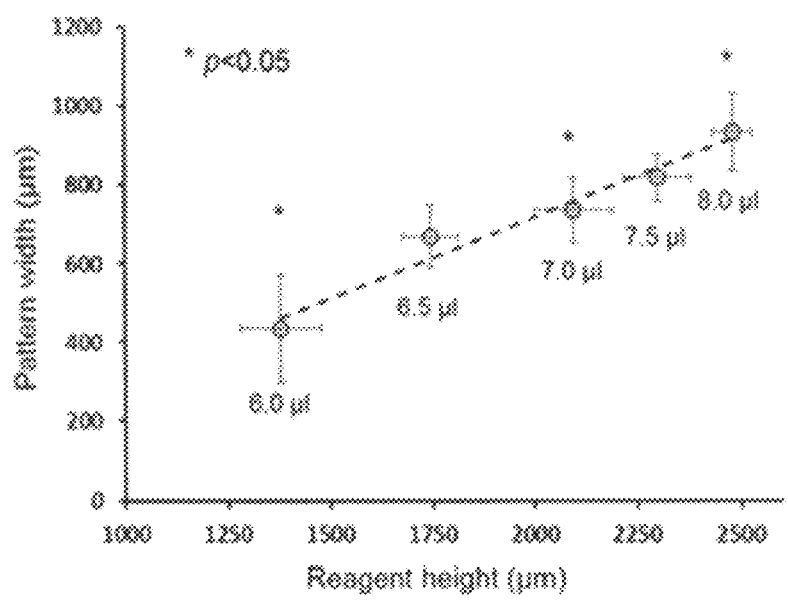

Each experimental volume was tested with a minimum of six replicates. To consider small volume inconsistencies due to manual loading of printing tips, tips were placed under a microscope before printing for imaging, and the reagent height above the capillary portion was measured (FIG. 10A). To eliminate the effect of printing tip speed on patterns breaking into droplets, individual patterns of FITC-DEX were printed at one arbitrarily selected speed that generated a pattern width within the stable regime (7.6 mm/s). FIG. 10B shows that, within the range of volumes studied, a consistent increase in the pattern width corresponded to an increase in the loaded volume at a constant lateral speed of the printing tip. A larger loaded volume translates into a larger height of the DEX phase in the tip and therefore, a larger potential energy (hydrostatic pressure). The potential-kinetic energy balance resulted in a dispensing speed of the DEX phase from the tip as $$v=\sqrt{2gh}, \quad [6]$$

where h denotes the height of the DEX phase in the printing tip and g is the gravitational acceleration. When the DEX phase is loaded to a greater height, a greater potential energy (hydrostatic pressure) translates into a larger kinetic energy that results in a faster dispensing speed, i.e., larger flow rate. Thus, at a constant printing tip speed, the dispensed DEX phase will cover a greater contact area with the surface at larger loaded volumes. The outcome was similar to printing with lower tip speeds at a constant volume (FIG. 12A). The loaded volume of the printing phase was found to provide another tunable means to change the lateral dimensions of printed patterns and spatially control placement of reagents and cells.

These results, however, cannot be applied to printing tips of different geometries. The particular tip under study was a standard gel-loading tip that featured a narrow, elongated end connected to a small conically-shaped "reservoir" above it (FIG. 7B, 7C; FIG. 10A). The range of volumes studied in this section only spanned the triangularly-shaped reservoir. Loaded volumes greater than 8 μl filled the tip above this reservoir region; however pattern width, did not change appreciably and remained more or less constant at 934.2±99 μm (data not shown in FIG. 10A). Because the interest was to generate narrow patterns only, volumes larger than 8 μl were not considered further. Also, larger loaded volumes dispensed larger amounts during insertion of the tip into the PEG phase, resulting in an blob at the beginning of patterns that made measurements of pattern width inconsistent for comparison.

Example 11

Analysis of the Effect of Printing Tip Diameter

The rate of the dispensing phase (i.e., the volumetric flow rate) was also dependent on the cross-sectional area of the printing tip through the following relation:

$$Q = vA, \quad [7]$$

Because ATPS printing is autonomous, varying the inner diameter can passively control the rate at which liquid dispenses and consequently how wide patterns spread. Tips used in studies on the printing tip speed, loaded volume, and surface type (discussed below) included standard gel-loading pipette tips with a measured capillary inner diameter of 312.9 μm (rounded to 300 μm). To systematically study the effect of other tip dimensions on patterns width, new tips with different capillary diameters were designed in Solid-Works (See Example 4). For each tip diameter, the pattern width decreased at higher speeds. This trend was more pronounced for 575 μm and 300 μm tips, where the patterns continuously decreased in size with increase in the printing tip speed. With the largest diameter tips (750 μm), the DEX phase tended to prematurely dispense upon insertion into the PEG phase solution before printing (horizontal motion of the tip) had started. To avoid this problem, the insertion speed of the printing tip was increased (through the z-axis motor) to 63.5 mm/s from 3.2 mm/s used with smaller diameter tips, but still yielded inconsistent dispensing at the onset of printing causing large variations in pattern width between samples. The inconsistent dispensing explained less significant decreases in patterns width with tips of diameter 750 μm. Among the tips studied, extruded tips with a measured 213.7 μm diameter (rounded to 200 μm), were the least likely to prematurely dispense at the onset of printing. Hence, patterns width exhibited less variations at each tested speed.

At a given speed, it was found that tips with a smaller inner diameter of 200 μm and 300 μm resulted in significantly finer patterns (p<0.05). The thinnest stable pattern was 322±64.5 μm obtained using an extruded tip of 200 μm at 17 mm/s. Further increase in the speed with the 200 μm tip resulted in unstable patterns. The fact that patterns printed with a 200 μm tip diameter were statistically smaller than patterns using a 300 μm tip diameter suggests that finer resolutions may be achievable by using tips of smaller diameters. However, the change in slope of pattern width printed with 200 μm at different speeds is much smaller than that for larger diameter tips. This implies that even if narrower patterns are obtained with smaller tip diameters, increasing the speed of the tip will not appreciably reduce it.

Example 12

The Effect of Surface Type on Printed Patterns

Figure 14E:
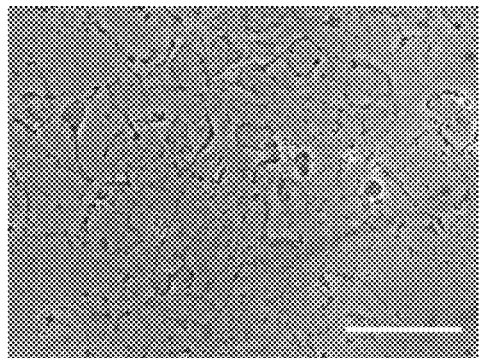
Figure 14F:
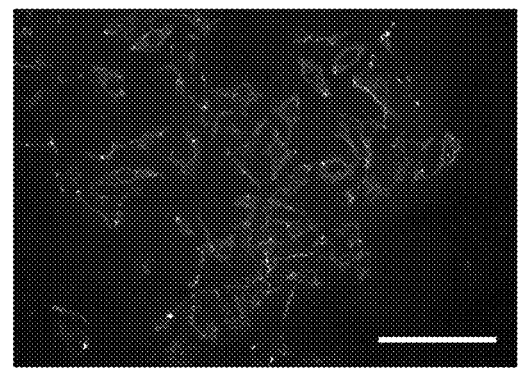

All characterization studies presented to this point were conducted on a confluent monolayer of cells as the printing surface (bio-paper) based on previous works that suggested pattern stability is partly due to interactions between the printing phase and the surface of living cells. While the capability of direct, non-contact printing on cells is a major advantage of the ATPS microtechnology, printing on other surfaces could broaden the utility of this approach. This capability would be important for tissue engineering applications that require the use of bioactive matrices for cell support and growth. Direct observations of the PEG-DEX interface revealed certain points where the interface became anchored to the cell monolayer. This observation prompted the question whether morphology of cell monolayer and its micrometer-scale roughness pins down and stabilizes printed patterns, or interactions between DEX phase and biological molecules on cells facilitate it. To address this question, several types of substrates were selected including molecularly smooth poly(D,L-lactic acid) (PDLA) films with a roughness of 1.9 nm, PDLA surfaces decorated with ordered microgrooves of 10 μm and 20 μm pitch (FIG. 14A), low cell-density surfaces (FIG. 14B), hydrophilic and hydrophobic polydimethyl siloxane (PDMS) replica of a monolayer of fixed cells (FIG. 14C), and a decellularized matrix with sub-micrometer roughness (FIG. 14E, 14F). See Example 2, above. The molecularly smooth PDLA surface, ordered microgrooved surface, and hydrophobic and hydrophilic cell layer replica surfaces were used to help elucidate the effect of surface roughness whereas the decellularized matrix could explain the contribution of biomolecules.

Figure 14G:
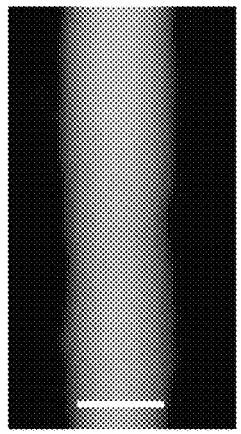
Figure 14H:
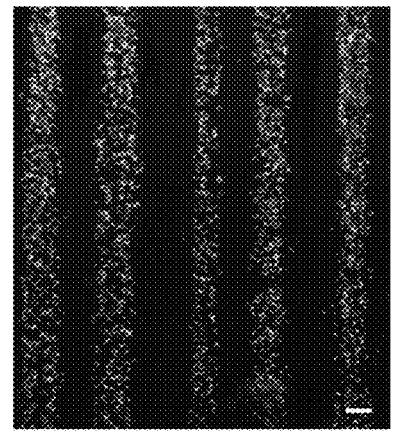

Linear patterns of FITC-DEX were printed on these substrates under similar conditions for the tip diameter (300 μm), loaded volume (8 μl), and printing tip speed (7.6 mm/s). To ensure that the tip speed did not affect pattern stability as in previous characterization studies, only a speed within the stable regime were used. All patterns printed onto the smooth PDLA, microgrooved PDLA, low cell-density and cell layer replica quickly became unstable and resolved into droplets (FIG. 14D). Contrarily, FITC-DEX patterns printed onto the decellularized matrix surface remained stable and intact over a period of 3 hrs. In addition, patterns on the decellularized matrix surface showed smoother edges than on a cell monolayer (FIG. 14G). In principle, the absence of curvatures can facilitate stable patterns of finer resolution. Decellularized matrices also supported linear cell patterns confirming the long-term stability of patterns (FIG. 14H). Altogether, this set of experiments indicated that the contribution of nanoscale and microscale surface roughness, ordered or random, is inadequate to stabilize linear patterns of DEX and suggests that biomolecules play a key role for maintaining DEX patterns stable for long time periods. It is known that pattern stability is driven, at least in part, by the affinity of the DEX molecules in the printed phase to select functional groups on the surface. The difference in the affinity of DEX molecules in the printed phase for different functional groups on the surface gave rise to surface energy barriers that pin the contact line of the printed DEX phase.

Decellularized matrices are biologically active surfaces that promote cell adhesion and growth and thus provide an appealing alternative to cell monolayer for printing with ATPS. Similar to a cell monolayer, a high-density matrix laid down by a 90-100% confluent layers of cells generate stable patterns of high-fidelity.

Example 13

Creating Heterocellular Niches in Multiple Configurations

Native tissues consist of multiple cell types organized into well-ordered microstructures where heterotypic cellular interactions play a crucial role in regulating tissue formation and function. Generating such well-organized constructs in vitro and replicating these interactions require a bottom-up approach, such as the ATPS microprinting, to enable controlled spatial arrangements of multiple cells in defined geometries. Duplex co-cultures of green and red fluorescently labeled mouse myoblast C2C12 cells were created in parallel, orthogonal, and acute geometries on cell layers and decellularized matrices. (See, Example 5). Co-cultures featured side-by-side linear patterns of two cell colors with defined interspacing. The process resulted in uniform linear patterns of one cell type sandwiched within linear patterns of a second cell type (FIG. 15A). Lateral dimension measurements revealed that patterns could be printed with a consistent size down to 348±10 μm without interspacing. For duplex cell printing in orthogonal and acute geometries, interspacing measurements between linear cell patterns light/dark has shown that spatial control is consistent down to ±19 μm.

Results from these experiments demonstrate the capability to both spatially and temporally control cell printing. Spatial control was realized through the computer interface that allowed printing cell patterns at computer-registered coordinates on the printing surface. Temporal control was, in this context, demonstrated by the ability to print cells of different colors at predefined time points: cell patterns in green were first printed and precisely four hours later, cell patterns in red were printed.

Example 14

Creating User-Defined Shapes

Bottom-up engineering of some tissues (e.g., liver) require controlled positioning of cells in complex geometries. Current cell printing technologies can accommodate multiple cell types but are limited in terms of creating user-defined viable cell patterns. Therefore, an experiment was designed to print user-defined patterns and show improvements in pattern generation based on the new automated platform. (See, Example 6) The narrow dispensing tip allowed greater control over dispensing to generate patterns of consistent size. A large loaded volume of 10 μl and slow speed of 3.2 mm/s allowed printing the shape "UA," to generate features that had a consistent size with droplets generated upon insertion and retraction of the tip. The arc in shape "U: could be programmed by carefully tuning the speed commands and incrementing small distances of the y-axis and x-axis motors. Programming such precise features like the arc were, however, not necessary because small droplets generated at the end of each line merged connecting lines in the shape of a curve. For printing the middle line feature in the A, since the length was half the distance of side line features and required the tip to insert at its beginning and retract at its end, small loaded volumes were used to prevent forming large droplets that would pull apart both ends from the line. In addition, since all three line features in the "A" were printed in less than one minute, droplets of 1 mm diameter in middle line feature could spread enough and disturb the fidelity of side lines.

To minimize the size of droplets at the beginning and end of linear patterns, printing was done with volumes starting at 5 μl, previously noted as the minimum volume needed to initiate autonomous dispensing upon insertion of the tip in the PEG phase. Loaded volumes below the selected 5.25 μl generated a small enough droplet 900 μm in diameter at the beginning of the line feature, but the lateral speed of the tip generated a line 335 μm in width. Due to the difference in size between the droplet and line feature, pressure gradients from local curvatures pulled apart the two features resulting in collapse of the line pattern. To minimize these curvatures, the volume was increased in increments of 0.5 μl until at 5.25 μl, a stable line could be printed. The resulting middle line in the 'A' of FIG. 15D shows droplets, 905 μm in diameter, connected to a linear feature, 625 μm in width.

Figure 15E:
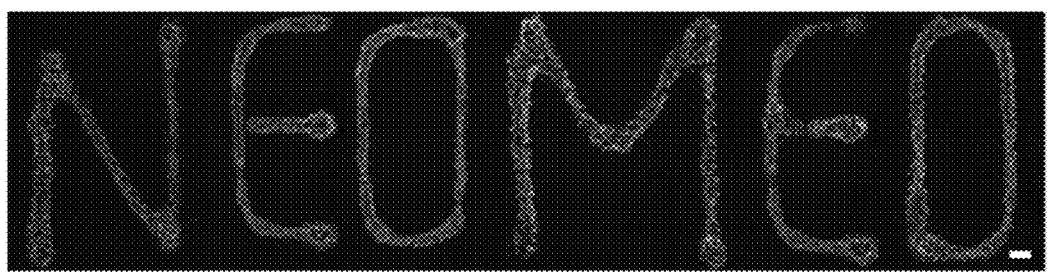

Measurements for pattern resolution on resulting images of "UA" and "NEOMED" at the selected printing conditions were 660±32 μm and 390±31 μm, respectively. Using a smaller loaded volume and higher speed (8 μl and 6.3 mm/s), "NEOMED," showed features of smaller sizes than "UA", but compromised their aesthetics as shown by the presence of blobs at the end of line features in N, E, and M (FIG. 15E). The autonomous nature of dispensing results in circular droplets close 1 mm in diameter, at the beginning and/or end of each pattern depending on whether or not the tip retracted after printing the feature. Several adjustments were made to generate a uniform width along each letter of the pattern. This included maximum insertion and retraction speeds (63.5 mm/s), continuous transition between Y-axis and Z-axis motors, and using lower tip speeds (6.3 mm/s). However, limitations of the current system still prevented letters of finer resolution to be printed without leaving a large blob at the beginning or end of printed patterns. As a result, conditions were set to print "UA" with features of similar sizes to circular droplets, and thereby generated patterns with relatively consistent lateral dimensions throughout.

In light of the foregoing, it should be appreciated that the present invention significantly advances the art by providing an automated cell bioprinter (and related methods) that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

APPENDIX A

```
data;
    Input innerd linewidth;
    datalines;
    750 1033
    750 1314
    750 1308
    750 760
    750 854
    750 919
    750 1344
    750 1014
    750 1049
    575 864
    575 740
    575 529
    575 599
    575 589
    300 470
    300 446
    300 400
    300 418
    300 305
    300 282
    ;
    Proc glm;
        class innerd;
```

```
            model linewidth = innerd;
            means innerd/tukey cldiff;
    title 'Compare Linewidth: across Inner Diameters';
proc gplot;
        plot linewidth*innerd;
proc boxplot;
        plot linewidth*innerd;
            title 'anova results';
    run;
```

The GLM Procedure

Tukey's Studentized Range (HSD) Test for 1 Linewidth

| Tukey's Studentized Range (HSD) Test for 1 in width | |
|---|---|
| Alpha | 0.05 |
| Error Degrees of Freedom | 17 |
| Error Mean Square | 27336.62 |
| Critical Value of Studentized Range | 3.62796 |

NOTE:
This test controls the Type I experimentwise error rate.

| innerd Comparison | Difference Between Means | Simultaneous 95% Confidence Limits | | |
|---|---|---|---|---|
| 750-575 | 401.91 | 165.33 | 638.49 | *** |
| 750-300 | 679.20 | 455.73 | 902.82 | *** |
| 575-750 | −401.91 | −638.49 | −165.33 | *** |
| 575-300 | 277.37 | 20.53 | 534.20 | *** |
| 300-750 | −679.28 | −902.82 | −455.73 | *** |
| 300-575 | −277.37 | −534.20 | −20.53 | *** |

Comparisons significant at the 0.05 level are indicated by ***.

Figure 17:
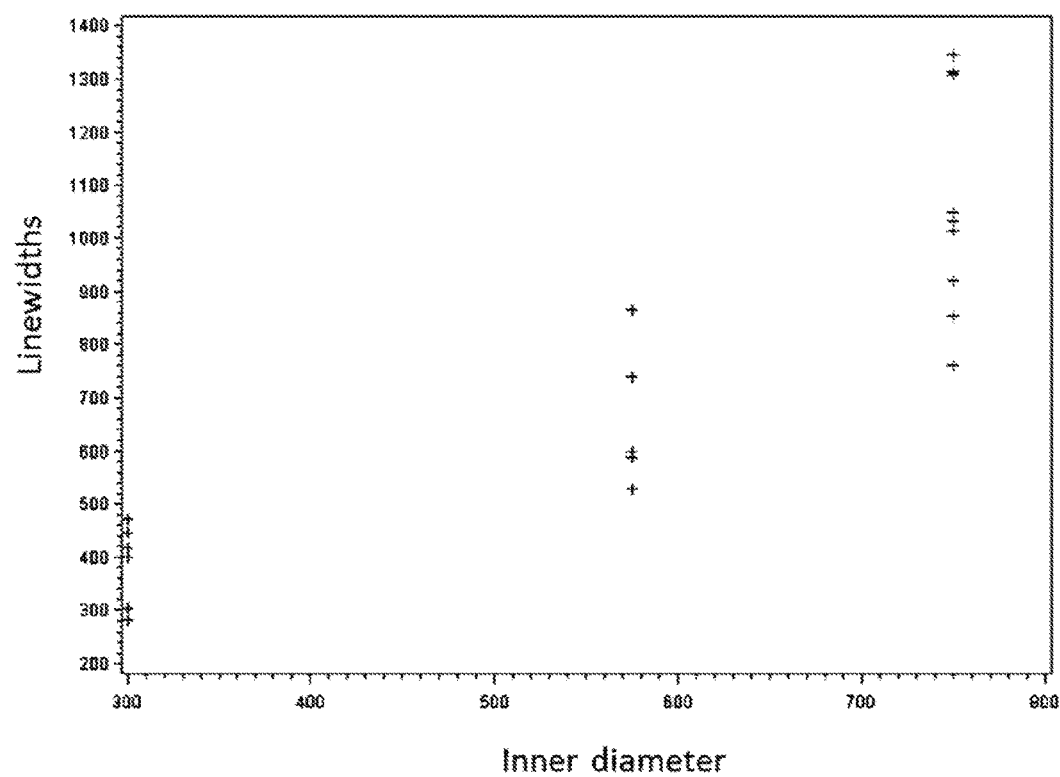
FIG. 17 is a graph comparing printed line widths to the inner diameter of printing tips according to at least one embodiment of the present invention. (See, Appendix A)

(See, FIG. 17)

APPENDIX B

%% This program signals the Z-axis motor to lower inside the dish, Z-axis
motor to perform a linear motion across the petri dish, the Z-axis motor to
retract out of the dish, and the x-axis motor to offset in preparation for the
next set of linear patterns.

```
F,        ;Enabel On-line mode
C,        ;Clear all commands from current program
S2M500,   ;Set Motor 2 (Z-axis) speed to 500 steps/sec (3.175 mm/s)
I2M3000,  ;Motor 2 (Z-axis) descends 3000 steps into PEG solution
S3M1200,  ;Set Motor 3 (Z-axis) speed to 1200 steps/sec (7.5 mm/s)
I3M5000,  ;Motor 3 (Z-axis) moves 5000 steps in the forward direction
S2M2000,  ;Set Motor 2 (Z-axis) speed to 2000 step/s (12.7 mm/s)
I2M-3000, ;Motor 2 (Z-axis) retracts 3000 steps to initial height
S3M2000,  ;Set motor 3 (Z-axis) speed to 2000 step/s (12.7 mm/s)
I3M-5000, ;Motor 3 (Z-axis) moves backward 5000 steps to starting point
I1M350,   ;Motor 1 (Z-axis) moves left 350 steps (2.22 mm)
R,        ;Run current program
```

Sample script to print a linear pattern for characterization studies.

%% This program signals the Z-axis motor to lower inside the dish, coordinated motion between Z-axis and x-axis motors in a *U*-shaped pattern, and the Z-axis motor to retract out of the dish.

```
F,        ;Enable On-line mode
C,        ;Clear all commands from previous programs
S2M700,   ;Set Motor 2 (Z-axis) speed to 700 steps/sec (4.44 mm/s)
I2M3000,  ;Motor 2 (Z-axis) descends to 3000 steps into PEG solution
S3M1000,  ;Set Motor 3 (Z-axis) speed to 1000 steps/s (6.35 mm/s)
I3M1170,  ;Motor 3 (Z-axis) moves 1170 steps (7.43 mm) in the forward direction
S1M1000,  ;Set Motor 1 (x-axis) speed to 1000 steps/s (6.35 mm/s)
I1M-660,  ;Motor 1 (x-axis) moves to the right 660 steps (4.2 mm)
S3M1000,  ;Set Motor 3 (Z-axis) speed to 1000 steps/s (635 mm/s)
S2M6000,  ;Set Motor 2 (Z-axis) to maximum speed of 6000 steps/s (38.1 mm/s)
I3M-1170, ;Move Motor 3 (Z-axis) in the backward direction 1170 steps (7.43 mm)
U77,      ;Start Continuous Index
I3M1170;  ;Motor 3 (Z-axis) moves 1170 steps (7.43 mm) in the backward direction
I2M-3000, ;Motor 2 (Z-axis) retracts 3000 steps to starting point
U99,      ;End Continuous Index
R         ;Run current program
```

%% This program signals the Z-axis motor to lower inside the dish, coordinated motion between Z-axis and x-axis motors in a backward U-shaped pattern, and the Z-axis motor to retract out of the dish.

```
F,        ;Enable On-line mode
C,        ;Clear all commands from previous programs
I1M-200,  ;Motor 1 (x-axis) moves to the right 200 steps (1.2 mm)
I3M1170,  ;Motor 3 (Z-axis) moves 1170 steps (7.43 mm) in the forward direction
S2M700,   ;Set Motor 2 (Z-axis) speed to 700 steps/sec (4.44 mm/s)
I2M3000;  ;Motor 2 (Z-axis) descends 3000 steps into PEG solution
S3M1000,  ;Set Motor 3 (Z-axis) speed to 1000 steps/s (6.35 mm/s)
I3M-1170, ;Motor 3 (Z-axis)moves 1170 steps (7.43 mm) in the backward direction
S1M1000,  ;Set Motor 1 (x-axis) speed to 1000 steps/s (6.35 mm/s)
I1M-660,  ;Motor 1 (x-axis) moves to the right 660 steps (4.2 mm)
S3M1000,  ;Set Motor 3 (Z-axis) speed to 1000 steps/s (6.35 mm/s)
S2M6000,  ;Set Motor 2 (Z-axis)to maximum speed of 6000 steps/s (38.1 mm/s)
I3M1170,  ;Move Motor 3 (Z-axis) in the forward direction 1170 steps (7.43 mm)
U77,      ;Start Continuous Index
I3M1170;  ;Motor 3 (Z-axis) moves 1170 steps (7.43 mm) in the backward direction
I2M-1000, ;Motor 2 (Z-axis) retracts 1000 steps
U99,      ;End Continuous Index
```

-continued

| | |
|---|---|
| R, | ;Run current program |

%%% This program signals the Z-axis motor to lower inside the dish, and the x-axis motor to complete the "A"-shaped pattern started with the previous program.

| | |
|---|---|
| F, | ;Enable On-line mode |
| C, | ;Clear all commands from previous programs |
| I3M-585, | ;Move Motor 3 (Z-axis) 585 steps (3.71 mm) in the backward direction |
| S2M1000, | ;Set Motor 2 speed to 1000 steps/sec (6.35 mm/s) |
| I2M1000, | ;Motor 2 (Z-axis) descends 1000 steps into PEG solution. |
| S1M800, | ;Set Motor 1 speed to 800 steps/sec (5.06 mm/s) |
| S2M1000, | ;Set Motor 2 speed to 1000 stepsts (6.35 mm/s) |
| U77; | ;Start Continuous Index |
| I1M660, | ;Motor 1 (x-axis) moves 660 steps to the left |
| I2M-3000, | ;Motor 2 (Z-axis) retracts 3000 steps to starting point |
| R, | ;Run current program |

Sample script to print user-defined shapes (i.e., UA).

APPENDIX C

```
%CIRCFIT Fits a circle in x,y plane
%
function [xc, yc, R, a] = circfit(x,y)
% Result is center point (yc,xc) and radius R. A is an optional
% output describing the circle's equation:
%
%    x^2+y^2+a(1)*x+a(2)*y+a(3)=0
% by Bucher izhak 25/oct/1991
n=length(x);   xx=x.*x; yy=y.*y; xy=x.*y;
A=[sum(x) sum(y) n;sum(xy) sum(yy) sum(y);sum(xx) sum(xy) sum(x)];
B=[-sum(xx+yy) ; -sum(xx.*y+yy.*y) ; -sum(xx.*x+xy.*y)];
a=A\B;
xc = -.5*a(1);
yc = -.5*a(2);
R  = sqrt((a(1)^2+a(2)^2)/4-a(3));
Make your lines verticle
%Have the circle fit and images with this file in the same directory
clc
%%%
%I=imread('C:\Users\ADSA\Desktop\David\old\1-50_1.63X.tif');
I=imread('C:\Users\ADSA\Desktop\6_R.tif');
%J=rgb2gray(I);
%K=imadjust(J);
J=I;
thresh=100;
sigma =2;
thresh_C=[0.15,0.3];
BW = edge(J,'canny',thresh_C,sigma);
figure
imshow(BW)
[obj,n]=bwlabel(BW,8);
object = zeros(1,n);
for k=1:n
        [Y,X]=find(obj==k);
        object(k) = length(Y);
        if object(k)<thresh
             BW(Y,X)=0;
        end
end
figure
imshow(BW)
impixelinfo
%%%
ymin=input('Please enter minimum Y: ')
ymax=input('Please enter maximum Y: ')
Scale=input('Please enter scale of imaging (Unit/Pixel) : ')
%%%
[r,c]=size(BW);
%CW=BW(ymin:ymax,5:c-floor(c/100)-2);
CW=BW(ymin:ymax,5:end);
figure
imshow(CW)
[obj,n]=bwlabel(CW,8);
% [Rtrim,Ctrim]=find(obj1>0);
% [r1,c1]=size(CW1);
% CW=zeros(r1,max(Ctrim)-min(Ctrim)+20);
```

-continued

APPENDIX C

```
% CW=CW1(1:end,min(Ctrim)-10:max(Ctrim)+10);
% [obj,n]=bwlabel(CW,8);
if n>2
    disp('error!')
    break;
else
    for i=1:n
        Y2=[ ];X2=[ ];X3=[ ];
        [Y2,X2]=find(obj==i);
        X3=X2-min(X2);
        [xc, yc, R, a] = circfit(X3,Y2);
        disp(R*Scale)
    end
end
I_initial=imread('C:\Users\ADSA\Desktop\P2.tif');
I=imread('C:\Users\ADSA\Desktop\P3.tif');
%J=rgb2gray(I);
%K=imadjust(J);
J=I;
thresh=100;
sigma =2;
thresh_C=[0.15,0.3];
BW = edge(J,'canny',thresh_C,sigma);
figure
imshow(BW)
[obj,n]=bwlabel(BW,8);
object = zeros(1,n);
for k=1:n
        [Y,X]=find(obj==k);
        object(k) = length(Y);
        if object(k)<thresh
             BW(Y,X)=0;
        end
end
figure
imshow(BW)
impixelinfo
I_initial(find(BW==1))=255;
figure
imshow(I_initial)
```

What is claimed is:

1. A method for the scaffold free bioprinting of cells comprising:
   A. providing an apparatus comprising a biomaterial surface upon which a plurality of cells are to be printed; one or more printing tips; a cartridge for holding said one or more printing tips; and a three-axis motion control system configured to move said cartridge in three dimensions with respect to said biomaterial surface;
   B. preparing an aqueous cell containing medium containing a first aqueous polymer;

C. loading said aqueous cell containing medium into the one or more printing tips;
D. preparing a second aqueous polymer solution, wherein said second aqueous polymer solution is less dense than and immiscible with said aqueous cell containing medium so that when the second aqueous polymer solution and said aqueous cell containing medium are mixed a partition is formed there between with the second aqueous polymer solution partitioned on the top and the aqueous cell containing medium on the bottom;
E. preparing the biomaterial surface comprising a decellularized matrix upon which the cells contained in said aqueous cell containing medium are to be printed;
F. covering said biomaterial surface with said second aqueous polymer solution to a depth of from about 1 to about 15 mm;
G. inserting said one or more printing tips into openings in said cartridge configured to receive said printing tips;
H. programming the three-axis motion control system to move said cartridge in three dimensions and at a predetermined speed to place the printing tips at specific predetermined locations as the aqueous cell containing medium is dispensed onto the biomaterial surface; and
I. dispensing the aqueous cell containing medium onto the biomaterial surface at specific predetermined locations and at a predetermined speed.

2. The method of claim 1 wherein said first aqueous polymer is dextran.

3. The method of claim 1 wherein said second aqueous polymer solution contains polyethylene glycol (PEG).

4. The method of claim 1 wherein the interfacial tension between the second aqueous polymer solution and the aqueous cell containing medium is from about 10 to about 14 $\mu$N/m.

5. The method of claim 1 wherein and the interfacial tension between the second aqueous polymer solution and the aqueous cell containing medium is 12 $\mu$N/m.

6. The method of claim 1 wherein the cells are selected from the cell types consisting of MDA-MB-231 breast cancer cells, C2C12 mouse myoblast cells, embryonic stem cells, and combinations thereof.

7. The method of claim 1 wherein the aqueous cell containing medium is dispensed from said printing tips by the force of gravity.

8. The method of claim 1 wherein said biomaterial surface comprises a high-density decellularized matrix laid down by a 95-100% confluent cell monolayer of any cell type.

9. The method of claim 1 further comprising dispensing the aqueous cell containing medium onto the biomaterial surface in one or more linear patterns.

10. The method of claim 1 further comprising:
I. allowing the cells in said aqueous cell containing medium to adhere to the biomaterial surface;
J. rinsing any unadhered cells off of said biomaterial surface;
K. covering said biomaterial surface and any cells adhered thereto with said second aqueous polymer solution to a depth of from about 1 to about 15 mm and
L. repeating steps A through H to apply a second layer of aqueous cell containing medium upon said biomaterial surface.

11. The method of claim 10 further comprising:
M. repeating steps A through L to apply additional cells upon said biomaterial surface and/or previously adhered cells to produce a three dimensional array of cells.

12. The method of claim 9 wherein said one or more linear patterns are reproducible.

13. The method of claim 9 wherein said one or more linear patterns are stable.

14. The method of claim 9 wherein each of said one or more linear patterns has a width of from about 254 $\mu$m to about 386 $\mu$m.

15. The method of claim 9 wherein each of said one or more linear patterns has a printing resolution of from 257.5 $\mu$m to about 386.5 $\mu$m.

16. The method of claim 9 wherein the Laplace Pressure is 130 mPa or less.

* * * * *